United States Patent
Schroder

(10) Patent No.: US 9,890,433 B2
(45) Date of Patent: Feb. 13, 2018

(54) COMPOSITIONS AND METHODS FOR DETECTING HUMAN PAPILLOMAVIRUS NUCLEIC ACID

(71) Applicant: Gen-Probe Incorporated, San Diego, CA (US)

(72) Inventor: Astrid R. W. Schroder, Encinitas, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 14/441,815

(22) PCT Filed: Oct. 11, 2013

(86) PCT No.: PCT/US2013/064519
§ 371 (c)(1),
(2) Date: May 8, 2015

(87) PCT Pub. No.: WO2014/059260
PCT Pub. Date: Apr. 17, 2014

(65) Prior Publication Data
US 2015/0307951 A1  Oct. 29, 2015

Related U.S. Application Data

(60) Provisional application No. 61/712,332, filed on Oct. 11, 2012.

(51) Int. Cl.
*C12Q 1/70* (2006.01)
*C12Q 1/68* (2006.01)

(52) U.S. Cl.
CPC .......... *C12Q 1/708* (2013.01); *C12Q 1/6865* (2013.01); *C12Q 2600/158* (2013.01)

(58) Field of Classification Search
CPC .. C12Q 1/708; C12Q 2600/16; C12Q 1/6837; C12Q 2531/113; C12Q 2600/118; C12Q 1/6813; B01J 2219/00576; Y10S 435/975
See application file for complete search history.

(56) References Cited

U.S. PATENT DOCUMENTS

| | | | |
|---|---|---|---|
| 8,658,397 B2 * | 2/2014 | Chen ...................... | C12Q 1/708 435/91.2 |
| 2011/0201516 A1 * | 8/2011 | Chen ...................... | C12Q 1/708 506/9 |
| 2015/0037785 A1 | 2/2015 | Gordon et al. | |

FOREIGN PATENT DOCUMENTS

| | | | |
|---|---|---|---|
| EP | 402132 | * | 6/1990 |
| EP | 0402132 A2 | | 12/1990 |
| WO | 89/02934 A1 | | 4/1989 |
| WO | WO8902934 | * | 4/1989 |
| WO | 94/26934 A2 | | 11/1994 |
| WO | 2006063065 A2 | | 6/2006 |
| WO | 2006116276 A2 | | 11/2006 |

OTHER PUBLICATIONS

AIPO Patent Examination Report No. 1, Australian Patent Application No. 2013205122, dated Feb. 3, 2015.
AIPO Patent Examination Report No. 2, Australian Patent Application No. 2013205122, dated Oct. 7, 2016.
SIPO Search Report, Chinese Patent Application No. 201380064307.1, dated Apr. 22, 2016.
SIPO First Office Action, Chinese Patent Application No. 201380064307.1, dated May 20, 2016.
SIPO Supplemental Search Report, Chinese Patent Application No. 201380064307.1, dated Mar. 15, 2017.
SIPO Second Office Action, Chinese Patent Application No. 201380064307.1, dated Mar. 23, 2017.
PCT Written Opinion, International Application No. PCT/US2013/064519, dated Apr. 23, 2014.
PCT International Search Report, International Application No. PCT/US2013/064519, dated Apr. 23, 2014.
PCT International Preliminary Report on Patentability, International Application No. PCT/US2013/064519, dated Apr. 14, 2015.
Getman et al., "Efficiency of the APTIMA HPV Assay for detection of the HPV RNA and DNA targets," Journal of Clinical Virology, 2009, vol. 45, S49-S54, American Society for Microbiology.
Hologic Package Insert, APTIMA HPV Assay, Part Nos. 303570/303585/303012 (2015).
Kraus et al., "Presence of E6 and E7 mRNA from Human Papillomavirus Types 16, 18, 31, 33, and 45 in the Majority of Cervical Carcimonas," Journal of Clinical Microbiology, 2006, vol. 44, No. 4, p. 1310-1317, American Society for Microbiology.
Ratman et al., "Clinical Performance of the PreTest HPV-Proofer E6/E7 mRNA Assay in Comparison with That of the Hybrid Capture 2 Test for Indentification of Woman at Risk of Cervical Cancer," Journal of Clinical Microbiology, 2010, vol. 48, No. 8, p. 2779-2785, American Society for Microbiology.
Song et al., "The Research Progress of the Molecular Biological Detection Method in Human Papillomavirus (HPV)," Journal of Chinese Practical Diagnosis and Therapy, vol. 5, Issue 26, Department of Pathology, Renmin Hospital, Henan Province, 450003.

* cited by examiner

*Primary Examiner* — Bao Li
(74) *Attorney, Agent, or Firm* — Jeffrey E. Landes

(57) ABSTRACT

Disclosed are nucleic acid oligomers, including amplification oligomers, capture probes, and detection probes, for detection of a human papillomavirus (HPV) nucleic acid. Also disclosed are methods of specific nucleic acid amplification and detection using the disclosed oligomers, as well as corresponding reaction mixtures and kits.

9 Claims, 2 Drawing Sheets

```
GTAAACTATAATGCCAAGTTTTAAAAAAGTAGGGTGTAACCGAAAGCGGT
TCAACCGAAAACGGTGCATATATAAAGCAAACATTTTGCAGTAAGGTACT
GCACGACTATGTTTCAAGACACTGAGGAAAAACCACGAACATTGCATGAT
TTGTGCCAAGCATTGGAGACAACTATACACAACATTGAACTACAGTGCGT
GGAATGCAAAAAACCTTTGCAACGATCTGAGGTATATGATTTTGCATTTG
CAGATTTAACAGTTGTATATAGAGGGAAATCCATTTGGAATATGTAAA
CTGTGTTTGCGGTTCTTATCTAAAATTAGTGAATATAGACATTATAATTA
TTCTGTATATGGAAATACATTAGAACAAACAGTTAAAAAACCTTTAAATG
AAATATTAATTAGGTGTATTATATGTCAAAGACCTTTGTGTCCTCAAGAA
AAAAAACGACATGTGGATTTAAACAAACGATTTCATAATATTTCGGGTCG
TTGGGCAGGGCGCTGTGCGGCGTGTTGGAGGTCCCGACGTAGAGAAACTG
CACTGTGACGTGTAAAAACGCCATGAGAGGACACAAGCCAACGTTAAAGG
AATATGTTTTAGATTTATATCCTGAACCAACTGACCTATACTGCTATGAG
CAATTAAGTGACAGCTCAGATGAGGATGAAGGCTTGGACCGGCCAGATGG
ACAAGCACAACCAGCCACAGCTGATTACTACATTGTAACCTGTTGTCACA
CTTGTAACACCACAGTTCGTTTATGTGTCAACAGTACAGCAAGTGACCTA
CGAACCATACAGCAACTACTTATGGGCACAGTGAATATTGTGTGCCCTAC
CTGTGCACAACAATAA
```

Figure 1

```
TAATAATAATAATCTTAGTATAAAAAAGTAGGGAGTGACCGAAAGTGGTG
AACCGAAAACGGTTGGTATATAAAGCACATAGTATTTTGTGCAAACCTAC
AGACGCCATGTTCAAAAATCCTGCAGAAAGACCTCGGAAATTGCATGAAC
TAAGCTCGGCATTGGAAATACCCTACGATGAACTAAGATTGAATTGTGTC
TACTGCAAAGGTCAGTTAACAGAAACAGAGGTATTAGATTTTGCATTTAC
AGATTTAACAATAGTATATAGGGACGACACACCACACGGAGTGTGTACAA
AATGTTTAAGATTTTATTCAAAAGTAAGTGAATTTAGATGGTATAGATAT
AGTGTGTATGGAACAACATTAGAAAAATTGACAAACAAAGGTATATGTGA
TTTGTTAATTAGGTGTATAACGTGTCAAAGACCGTTGTGTCCAGAAGAAA
AACAAAGACATTTGGATAAAAGAAACGATTCCACAACATAGGAGGAAGG
TGGACAGGACGTTGCATAGCATGTTGGAGAAGACCTCGTACTGAAACCCA
AGTGTAAACATGCGTGGAGAAACACCTACGTTGCAAGACTATGTGTTAGA
TTTGCAACCTGAGGCAACTGACCTCCACTGTTATGAGCAATTACCCGACA
GCTCAGATGAGGAGGATGTCATAGACAGTCCAGCTGGACAAGCAGAACCG
GACACATCCAATTACAATATCGTTACCTTTTGTTGTCAGTGTAAGTCTAC
ACTTCGTTTGTGTGTACAGAGCACACAAGTAGATATTCGCATATTGCAAG
AGCTGTTAATGGGCTCATTTGGAATCGTGTGCCCCAACTGTTCTACTAGA
CTGTAA
```

Figure 2

SEQUENCE LISTING

```
<160> NUMBER OF SEQ ID NOS: 161

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
tcaagacact gaggaaaaac c                                              21
```

```
<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
gtttcaagac actgagga                                                 18

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 3
tatgtttcaa gacactgagg a                                             21

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
acgactatgt ttcaagacac tgag                                          24

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
gactatgttt caagacactg ag                                            22

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ctgcacgact atgtttcaag                                               20

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 7
gtactgcacg actatgtttc aaga                                          24

<210> SEQ ID NO 8
<211> LENGTH: 19
<212> TYPE: DNA
<213> ORGANISM: Artificial Sequence
<220> FEATURE:
```

<223> OTHER INFORMATION: synthetic oligonucleotide

<400> SEQUENCE: 8
agtaaggtac tgcacgact                                                    19

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
tagttgtctc caatgcttg                                                    19

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
atgttgtgta tagttgtctc c                                                 21

<210> SEQ ID NO 11
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 11
tagttcaatg ttgtgtatag ttgt                                              24

<210> SEQ ID NO 12
<211> LENGTH: 26
<212> TYPE: DNA
<213> ORGANISM: Artificial Sequence
<220> FEATURE:
<223> OTHER INFORMATION: Synthetic DNA and/or RNA oligonucleotide

<400> SEQUENCE: 12
ctgtagttca atgttgtgta tagttg                                            26

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 13
gcactgtagt tcaatgttgt g                                                 21

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 14
cacgcactgt agttcaatg                                                    19

```
<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 15
cattccacgc actgtagttc a                                              21

<210> SEQ ID NO 16
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 16
tgcattccac gcactgtagt tca                                            23

<210> SEQ ID NO 17
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 17
aatttaatac gactcactat agggagatag ttgtctccaa tgcttg                   46

<210> SEQ ID NO 18
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 18
aatttaatac gactcactat agggagaatg ttgtgtatag ttgtctcc                 48

<210> SEQ ID NO 19
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 19
aatttaatac gactcactat agggagatag ttcaatgttg tgtatagttg t             51

<210> SEQ ID NO 20
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 20
aatttaatac gactcactat agggagactg tagttcaatg ttgtgtatag ttg           53

<210> SEQ ID NO 21
<211> LENGTH: 48
<212> TYPE: DNA
<213> ORGANISM: Artificial Sequence
<220> FEATURE:
<223> OTHER INFORMATION: synthetic oligonucleotide
```

<400> SEQUENCE: 21
aatttaatac gactcactat agggagagca ctgtagttca atgttgtg            48

<210> SEQ ID NO 22
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 22
aatttaatac gactcactat agggagacac gcactgtagt tcaatg              46

<210> SEQ ID NO 23
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 23
aatttaatac gactcactat agggagacat tccacgcact gtagttca            48

<210> SEQ ID NO 24
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 24
aatttaatac gactcactat agggagatgc attccacgca ctgtagttca          50

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
atgagcaatt acccgacagc                                           20

<210> SEQ ID NO 26
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 26
gagcaattac ccgacagc                                             18

<210> SEQ ID NO 27
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 27
tacccgacag ctcagatga                                            19

<210> SEQ ID NO 28
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 28
acccgacagc tcagatgagg                                            20

<210> SEQ ID NO 29
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 29
gacagctcag aggaggagga tg                                         22

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
gctcagatga ggaggatgtc                                            20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
cagatgagga ggatgtcata                                            20

<210> SEQ ID NO 32
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 32
atgaggagga tgtcatagac a                                          21

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
aggaggatgt catagacagt c                                          21

<210> SEQ ID NO 34
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 34

```
cacacaaacg aagtgtagac ttacactgac                                      30

<210> SEQ ID NO 35
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 35
gtgtagactt acactgacaa ca                                              22

<210> SEQ ID NO 36
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 36
cgaagtgtag acttacactg aca                                             23

<210> SEQ ID NO 37
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 37
caaacgaagt gtagacttac ac                                              22

<210> SEQ ID NO 38
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 38
cacacaaacg aagtgtagac t                                               21

<210> SEQ ID NO 39
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 39
ctctgtacac acaaacgaag t                                               21

<210> SEQ ID NO 40
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 40
gtgtgctctg tacacacaaa cg                                              22

<210> SEQ ID NO 41
<211> LENGTH: 22
<212> TYPE: DNA
<213> ORGANISM: Artificial Sequence
```

```
<220> FEATURE:
<223> OTHER INFORMATION: synthetic oligonucleotide

<400> SEQUENCE: 41
gaatatctac ttgtgtgctc tg                                          22

<210> SEQ ID NO 42
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 42
aatttaatac gactcactat agggagacac acaaacgaag tgtagactta cactgac    57

<210> SEQ ID NO 43
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 43
aatttaatac gactcactat agggagagtg tagacttaca ctgacaaca             49

<210> SEQ ID NO 44
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 44
aatttaatac gactcactat agggagacga agtgtagact tacactgaca            50

<210> SEQ ID NO 45
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 45
aatttaatac gactcactat agggagacaa acgaagtgta gacttacac             49

<210> SEQ ID NO 46
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 46
aatttaatac gactcactat agggagacac acaaacgaag tgtagact              48

<210> SEQ ID NO 47
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 47
aatttaatac gactcactat agggagactc tgtacacaca aacgaagt              48
```

<210> SEQ ID NO 48
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 48
aatttaatac gactcactat agggagagtg tgctctgtac acacaaacg         49

<210> SEQ ID NO 49
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 49
aatttaatac gactcactat agggagagaa tatctacttg tgtgtgctc         49

<210> SEQ ID NO 50
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 50
aaauguuugc uuuauauaug cacc                                    24

<210> SEQ ID NO 51
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 51
aaauguuugc uuuauauaug cacctttaaa aaaaaaaaa aaaaaaaaa aaaaaaa   57

<210> SEQ ID NO 52
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 52
gcucauaaca guggagguca guugccuc                                28

<210> SEQ ID NO 53
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 53
gcucauaaca guggagguca guugccuctt taaaaaaaaa aaaaaaaaa aaaaaaaaa   60 a                                                                61

<210> SEQ ID NO 54
<211> LENGTH: 20
<212> TYPE: DNA
<213> ORGANISM: Artificial Sequence -continued

```
<220> FEATURE:
<223> OTHER INFORMATION: synthetic oligonucleotide

<400> SEQUENCE: 54
ccacgaacau ugcaugauuu                                          20

<210> SEQ ID NO 55
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 55
ccacgaacau ugcaugauuu gug                                      23

<210> SEQ ID NO 56
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 56
cgaacauugc augauuugug c                                        21

<210> SEQ ID NO 57
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 57
ccacgaacau ugcaugauuu gugcc                                    25

<210> SEQ ID NO 58
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 58
cgaacauugc augauuugug cc                                       22

<210> SEQ ID NO 59
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 59
cagcuggaca agcagaaccg gac                                      23

<210> SEQ ID NO 60
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 60
agcuggacaa gcagaaccgg ac                                       22
```

```
<210> SEQ ID NO 61
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 61
agcuggacaa gcagaaccgg aca                                               23

<210> SEQ ID NO 62
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 62
cagcuggaca agcagaaccg gaca                                              24

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
cuggacaagc agaaccggac                                                   20

<210> SEQ ID NO 64
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 64
cuggacaagc agaaccggac acauc                                             25

<210> SEQ ID NO 65
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 65
cuggacaagc agaaccggac acaucc                                            26

<210> SEQ ID NO 66
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 66
agtaaggtac tgcacgacta tgtttcaaga cactgaggaa aaacc                       45

<210> SEQ ID NO 67
<211> LENGTH: 8
<212> TYPE: DNA
<213> ORGANISM: Artificial Sequence
<220> FEATURE:
<223> OTHER INFORMATION: Amp oligo core hybridizing sequence
```

```
<400> SEQUENCE: 67 gtttcaag                                                             8

<210> SEQ ID NO 68
<211> LENGTH: 8
<212> TYPE: DNA
<213> ORGANISM: Artificial Sequence
<220> FEATURE:
<223> OTHER INFORMATION: Amp oligo core hybridizing sequence

<400> SEQUENCE: 68 acactgag                                                             8

<210> SEQ ID NO 69
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 69
ctgcacgact                                                          10

<210> SEQ ID NO 70
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 70
tgcattccac gcactgtagt tcaatgttgt gtatagttgt ctccaatgct tg           52

<210> SEQ ID NO 71
<211> LENGTH: 9
<212> TYPE: DNA
<213> ORGANISM: Artificial Sequence
<220> FEATURE:
<223> OTHER INFORMATION: Amp oligo core hybridizing sequence

<400> SEQUENCE: 71 ctgtagttc                                                            9

<210> SEQ ID NO 72
<211> LENGTH: 8
<212> TYPE: DNA
<213> ORGANISM: Artificial Sequence
<220> FEATURE:
<223> OTHER INFORMATION: Amp oligo core hybridizing sequence

<400> SEQUENCE: 72 atgttgtg                                                             8

<210> SEQ ID NO 73
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 73
agttgtctcc                                                          10

<210> SEQ ID NO 74
```

```
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 74
atgagcaatt acccgacagc tcagakgagg aggatgtcat agacagtc        48

<210> SEQ ID NO 75
<211> LENGTH: 9
<212> TYPE: DNA
<213> ORGANISM: Artificial Sequence
<220> FEATURE:
<223> OTHER INFORMATION: Amp oligo core hybridizing sequence

<400> SEQUENCE: 75 aggaggatg                                                    9

<210> SEQ ID NO 76
<211> LENGTH: 9
<212> TYPE: DNA
<213> ORGANISM: Artificial Sequence
<220> FEATURE:
<223> OTHER INFORMATION: Amp oligo core hybridizing sequence

<400> SEQUENCE: 76 cagakgagg                                                    9

<210> SEQ ID NO 77
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 77
acccgacagc                                                  10

<210> SEQ ID NO 78
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 78
gaatatctac ttgtgtgctc tgtacacaca aacgaagtgt agacttacac tgacaaca    58

<210> SEQ ID NO 79
<211> LENGTH: 9
<212> TYPE: DNA
<213> ORGANISM: Artificial Sequence
<220> FEATURE:
<223> OTHER INFORMATION: Amp oligo core hybridizing sequence

<400> SEQUENCE: 79 gtgtagact                                                    9

<210> SEQ ID NO 80
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 80
```

| cacacaaacg | 10 |

<210> SEQ ID NO 81
<211> LENGTH: 9
<212> TYPE: DNA
<213> ORGANISM: Artificial Sequence
<220> FEATURE:
<223> OTHER INFORMATION: Amp oligo core hybridizing sequence

<400> SEQUENCE: 81

| tgtgctctg | 9 |

<210> SEQ ID NO 82
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 82

| aatttaatac gactcactat agggaga | 27 |

<210> SEQ ID NO 83
<211> LENGTH: 866
<212> TYPE: DNA
<213> ORGANISM: Human papillomavirus type 33
<300> PUBLICATION INFORMATION:
<308> DATABASE ACCESSION NUMBER: M12732.1  GI:333049
<309> DATABASE ENTRY DATE: 1994-03-21
<313> RELEVANT RESIDUES IN SEQ ID NO: (1)..(866)

<400> SEQUENCE: 83

| gtaaactata atgccaagtt ttaaaaaagt agggtgtaac cgaaagcggt tcaaccgaaa | 60 |
| acggtgcata tataaagcaa acattttgca gtaaggtact gcacgactat gtttcaagac | 120 |
| actgaggaaa aaccacgaac attgcatgat ttgtgccaag cattggagac aactatacac | 180 |
| aacattgaac tacagtgcgt ggaatgcaaa aaacctttgc aacgatctga ggtatatgat | 240 |
| tttgcatttg cagatttaac agttgtatat agagagggaa atccatttgg aatatgtaaa | 300 |
| ctgtgtttgc ggttcttatc taaaattagt gaatatagac attataatta ttctgtatat | 360 |
| ggaaatacat tagaacaaac agttaaaaaa cctttaaatg aaatattaat taggtgtatt | 420 |
| atatgtcaaa gacctttgtg tcctcaagaa aaaaacgac atgtggattt aaacaaacga | 480 |
| tttcataata tttcgggtcg ttgggcaggg cgctgtgcgg cgtgttggag gtcccgacgt | 540 |
| agagaaactg cactgtgacg tgtaaaaacg ccatgagagg acacaagcca acgttaaagg | 600 |
| aatatgtttt agatttatat cctgaaccaa ctgacctata ctgctatgag caattaagtg | 660 |
| acagctcaga tgaggatgaa ggcttggacc ggccagatgg acaagcacaa ccagccacag | 720 |
| ctgattacta cattgtaacc tgttgtcaca cttgtaacac cacagttcgt ttatgtgtca | 780 |
| acagtacagc aagtgaccta cgaaccatac agcaactact tatgggcaca gtgaatattg | 840 |
| tgtgccctac ctgtgcacaa caataa | 866 |

<210> SEQ ID NO 84
<211> LENGTH: 856
<212> TYPE: DNA
<213> ORGANISM: Human papillomavirus type 31
<300> PUBLICATION INFORMATION:
<308> DATABASE ACCESSION NUMBER: HQ537666.1  GI:337237882
<309> DATABASE ENTRY DATE: 2011-06-27
<313> RELEVANT RESIDUES IN SEQ ID NO: (1)..(856)

<400> SEQUENCE: 84

| | | |
|---|---|---|
| taataataat aatcttagta taaaaaagta gggagtgacc gaaagtggtg aaccgaaaac | 60 | |
| ggttggtata taaagcacat agtattttgt gcaaacctac agacgccatg ttcaaaaatc | 120 | |
| ctgcagaaag acctcggaaa ttgcatgaac taagctcggc attggaaata ccctacgatg | 180 | |
| aactaagatt gaattgtgtc tactgcaaag gtcagttaac agaaacagag gtattagatt | 240 | |
| ttgcatttac agatttaaca atagtatata gggacgacac accacacgga gtgtgtacaa | 300 | |
| aatgtttaag attttattca aaagtaagtg aatttagatg gtatagatat agtgtgtatg | 360 | |
| gaacaacatt agaaaaattg acaaacaaag gtatatgtga tttgttaatt aggtgtataa | 420 | |
| cgtgtcaaag accgttgtgt ccagaagaaa aacaaagaca tttggataaa aagaaacgat | 480 | |
| tccacaacat aggaggaagg tggacaggac gttgcatagc atgttggaga agacctcgta | 540 | |
| ctgaaaccca agtgtaaaca tgcgtggaga aacacctacg ttgcaagact atgtgttaga | 600 | |
| tttgcaacct gaggcaactg acctccactg ttatgagcaa ttacccgaca gctcagatga | 660 | |
| ggaggatgtc atagacagtc cagctggaca agcagaaccg gacacatcca attacaatat | 720 | |
| cgttaccttt tgttgtcagt gtaagtctac acttcgtttg tgtgtacaga gcacacaagt | 780 | |
| agatattcgc atattgcaag agctgttaat gggctcattt ggaatcgtgt gccccaactg | 840 | |
| ttctactaga ctgtaa | 856 | |

<210> SEQ ID NO 85
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 85
aggaggatgt catagacaag tc                                          22

<210> SEQ ID NO 86
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 86
aatttaatac gactcactat agggagagaa tatctacttg tgtgctc                47

<210> SEQ ID NO 87
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 87
gaatatctac ttgtgtgctc                                             20

<210> SEQ ID NO 88
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 88
gctcataaca gtggaggtca gttgcctctt taaaaaaaaa aaaaaaaaa aaaaaaaaa   60

-continued

```
a                                                              61

<210> SEQ ID NO 89
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 89
ctccaacacg ctgcacagcg ccctgtttaa aaaaaaaaa aaaaaaaaa aaaaaaa      58

<210> SEQ ID NO 90
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 90
gtgcacagat caggtagctt gtagggtcgt ttaaaaaaaa aaaaaaaaaa aaaaaaaaaa  60
aa                                                             62

<210> SEQ ID NO 91
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 91
gctcataaca gtggaggtca gttgcctctt taaaaaaaaa aaaaaaaaaa aaaaaaaaa   60 a                                                              61

<210> SEQ ID NO 92
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 92
gctcataaca gtggaggtca gttgcctc                                 28

<210> SEQ ID NO 93
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 93
gugcacagau cagguagcuu guagggucgu uuaaaaaaaa aaaaaaaaaa aaaaaaaaaa  60
aa                                                             62

<210> SEQ ID NO 94
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 94
```
gugcacagau cagguagcuu guagggucg                                29

<210> SEQ ID NO 95
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 95
ctccaacacg ctgcacagcg ccctg                                    25

<210> SEQ ID NO 96
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 96
gtgcacagat caggtagctt gtagggtcg                                29

<210> SEQ ID NO 97
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 97
gctcataaca gtggaggtca gttgcctc                                 28

<210> SEQ ID NO 98
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 98
ttaartgaca gctcagakga ggakgatgaa atagatggtc                    40

<210> SEQ ID NO 99
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 99
ctcagakgag gakg                                                14

<210> SEQ ID NO 100
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 100
gtgacagctc agatgaggat g                                        21

<210> SEQ ID NO 101
<211> LENGTH: 22
<212> TYPE: DNA
<213> ORGANISM: Artificial Sequence

```
<220> FEATURE:
<223> OTHER INFORMATION: synthetic oligonucleotide

<400> SEQUENCE: 101
gacagctcag akgaggagga tg                                              22

<210> SEQ ID NO 102
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 102
ctcagakgag gakgatgaaa tagatgg                                         27

<210> SEQ ID NO 103
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 103
rtgacagctc agakgaggak gatg                                            24

<210> SEQ ID NO 104
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 104
gacagctcag atgaggagga tg                                              22

<210> SEQ ID NO 105
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 105
tgacagctca gakgaggakg atgaaatag                                       29

<210> SEQ ID NO 106
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 106
caatattgta accttttgtt gcaagtgtga ctctacgctt cggttgtgcg                50

<210> SEQ ID NO 107
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 107
agagtcacac ttg                                                        13
```

<210> SEQ ID NO 108
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 108
aatttaatac gactcactat agggagaact tgcaacaaaa ggttac        46

<210> SEQ ID NO 109
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 109
aatttaatac gactcactat agggagaaca cttgcaacaa aaggttacaa tattg        55

<210> SEQ ID NO 110
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 110
aatttaatac gactcactat agggagaaga gtcacacttg caacaaaag        49

<210> SEQ ID NO 111
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 111
aatttaatac gactcactat agggagaaga gtcacacttg caacaaaagg        50

<210> SEQ ID NO 112
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 112
aatttaatac gactcactat agggagagca caaccgaagc gtagagtc        48

<210> SEQ ID NO 113
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 113
aatttaatac gactcactat agggagacgc acaaccgaag cgtagagtca cacttgc        57

<210> SEQ ID NO 114
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 114
aatttaatac gactcactat agggagaaag cgtagagtca cacttgc       47

<210> SEQ ID NO 115
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 115
aatttaatac gactcactat agggagagca acaaaaggtt acaatattg     49

<210> SEQ ID NO 116
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 116
aatttaatac gactcactat agggagagaa gcgtagagtc acacttg       47

<210> SEQ ID NO 117
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 117
caacaaaagg ttac                                           14

<210> SEQ ID NO 118
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 118
acttgcaaca aaaggttac                                      19

<210> SEQ ID NO 119
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 119
acacttgcaa caaaaggtta caatattg                            28

<210> SEQ ID NO 120
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 120
agagtcacac ttgcaacaaa ag                                  22

<210> SEQ ID NO 121

<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 121
agagtcacac ttgcaacaaa agg                                              23

<210> SEQ ID NO 122
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 122
gcacaaccga agcgtagagt c                                                21

<210> SEQ ID NO 123
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 123
cgcacaaccg aagcgtagag tcacacttgc                                       30

<210> SEQ ID NO 124
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 124
aagcgtagag tcacacttgc                                                  20

<210> SEQ ID NO 125
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 125
gcaacaaaag gttacaatat tg                                               22

<210> SEQ ID NO 126
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 126
gaagcgtaga gtcacacttg                                                  20

<210> SEQ ID NO 127
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 127
cagckggaca agcagaaccg gac                                    23

<210> SEQ ID NO 128
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 128
cgacgagccg aaccac                                            16

<210> SEQ ID NO 129
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 129
cgacgagccg aaccaca                                           17

<210> SEQ ID NO 130
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 130
gacgagccga accaca                                            16

<210> SEQ ID NO 131
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 131
cgacgagccg aaccacaa                                          18

<210> SEQ ID NO 132
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 132
gacgagccga accacaa                                           17

<210> SEQ ID NO 133
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 133
acgagccgaa ccacaa                                            16

<210> SEQ ID NO 134
<211> LENGTH: 46
<212> TYPE: DNA

<213> ORGANISM: Artificial Sequence
<220> FEATURE:
<223> OTHER INFORMATION: synthetic oligonucleotide

<400> SEQUENCE: 134
aatttaatac gactcactat agggagagtt cagaaacagc tgctgg    46

<210> SEQ ID NO 135
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 135
aatttaatac gactcactat agggagagtg ttcagaaaca gctgctgg    48

<210> SEQ ID NO 136
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 136
aatttaatac gactcactat agggagaggg tgttcagaaa cagctgctgg    50

<210> SEQ ID NO 137
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 137
aatttaatac gactcactat agggagaggg tgttcagaaa cagctg    46

<210> SEQ ID NO 138
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 138
aatttaatac gactcactat agggagaaca cacaaaggac agggt    45

<210> SEQ ID NO 139
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 139
aatttaatac gactcactat agggagagac acacaaagga cagggt    46

<210> SEQ ID NO 140
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 140
aatttaatac gactcactat agggagagca caccacggac acacaaagg    49

<210> SEQ ID NO 141
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 141
aatttaatac gactcactat agggagacac accacggaca cacaaaggac          50

<210> SEQ ID NO 142
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 142
aatttaatac gactcactat agggagacac accacggaca cacaaag             47

<210> SEQ ID NO 143
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 143
ccagcagctg tttctgaaca ccctgtcctt tgtgtgtccg tggtgtgc             48

<210> SEQ ID NO 144
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 144
gttcagaaac agctgctgg                                            19

<210> SEQ ID NO 145
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 145
gtgttcagaa acagctgctg g                                         21

<210> SEQ ID NO 146
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 146
gggtgttcag aaacagctgc tgg                                       23

<210> SEQ ID NO 147
<211> LENGTH: 19
<212> TYPE: DNA
<213> ORGANISM: Artificial Sequence
<220> FEATURE:

```
<223> OTHER INFORMATION: synthetic oligonucleotide

<400> SEQUENCE: 147
gggtgttcag aaacagctg                                                      19

<210> SEQ ID NO 148
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 148
acacacaaag gacagggt                                                       18

<210> SEQ ID NO 149
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 149
gacacacaaa ggacagggt                                                      19

<210> SEQ ID NO 150
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 150
gcacaccacg gacacacaaa gg                                                  22

<210> SEQ ID NO 151
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 151
cacaccacgg acacacaaag gac                                                 23

<210> SEQ ID NO 152
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 152
cacaccacgg acacacaaag                                                     20

<210> SEQ ID NO 153
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 153
gcagacgacc uucgagcauu c                                                   21
```

```
<210> SEQ ID NO 154
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 154
cgucugcuga gcuuucua                                                     18

<210> SEQ ID NO 155
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 155
guaguagaaa gcucagcaga cgacc                                             25

<210> SEQ ID NO 156
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 156
guagaaaccu cgc                                                          13

<210> SEQ ID NO 157
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (18)..(18)
<223> OTHER INFORMATION: n is a or g or c or t/u, unknown, or other.

<400> SEQUENCE: 157
guagagagcu cggcaganga c                                                 21

<210> SEQ ID NO 158
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 158
gugugacggc agaauugagc                                                   20

<210> SEQ ID NO 159
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 159
ugugugugug uuguaagugu                                                   20

<210> SEQ ID NO 160
<211> LENGTH: 15
<212> TYPE: DNA
```

```
<213> ORGANISM: Artificial Sequence
<220> FEATURE:
<223> OTHER INFORMATION: synthetic oligonucleotide

<400> SEQUENCE: 160
ucuucugccg agcuc                                                     15

<210> SEQ ID NO 161
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 161
guagagagcu cggcagagga c                                              21
```

COMPOSITIONS AND METHODS FOR DETECTING HUMAN PAPILLOMAVIRUS NUCLEIC ACID

PRIORITY

This application claims the benefit of priority to the following applications: U.S. Provisional Application No. 61/712,332 filed 11 Oct. 2012, the entire content of which is hereby incorporated herein by reference.

BACKGROUND OF THE INVENTION

Human papillomaviruses (HPV) target epithelial tissues for infection and are etiological agents of a variety of cancers, predominantly squamous cell carcinomas and adenocarcinomas. HPV-associated cancers include those of the head and neck (larynx, oral cavity, oropharynx, tonsils, and esophagus), respiratory tissue, breast, skin, cervix, and anus. Although HPV infection is considered a necessary factor in development of some cancers, other factors may also affect carcinogenesis (Braakhuis et al., *J. Natl. Cancer Inst.* 96:998-1006, 2004; Dahlstrand et al., *Anticancer Res.* 24:1829-35, 2004; Daling et al., *Cancer* 101:270-80, 2004; Ha et al., *Crit. Rev. Oral Biol. Med.* 15:188-96, 2004; Hafkamp et al., *Acta Otolaryngol.* 124:520-6, 2004; Harwood et al., *Br. J. Dermatol.* 150:949-57, 2004; Rees et al., *Clin. Otolaryngol.* 29:301-6, 2004; Widschwendter et al., *J. Clin. Virol.* 31:292-7, 2004).

At least 77 different types of HPV have been identified. Of those, HPV16 and HPV18 are frequently linked to a variety of HPV-associated cancers, but the risk level associated with a HPV type may vary with different forms of papilloma-associated cancers. The pathogenesis of human papillomaviruses in epithelia has been studied to elucidate the link of HPV infection to cancers. HPV infects basal layer cells of stratified epithelia where they become established as multi-copy episomes or integrated genomes, by which the viral DNA is replicated with cellular chromosomes (reviewed by Longworth et al., *Microbiol. Mol. Biol. Rev.* 68:362-72, 2004). At cell division, a daughter cell migrates away from the basal layer and undergoes differentiation in which HPV vegetative viral replication and late-gene expression are activated to produce progeny HPV. Although an infected individual's immune system may clear the HPV infection, usually within 1 to 2 years, infected basal cells may persist for decades. HPV infection may lead to chromosomal instability and aneupolidy that may favor HPV integration (Melsheimer et al., *Clin. Cancer Res.* 10:3059-63, 2004; Reidy et al., *Laryngoscope* 114:1906-9, 2004). During HPV genome integration, the HPV E2 gene may be destroyed, resulting in deregulated expression of the HPV E6/E7 oncogenes that encode oncoproteins that target the regulatory proteins pRb and p53. Thus, a cascade of events that modulate cellular regulation may result in carcinogenesis (Braun et al., *Cancer Lett.* 209:37-49, 2004; Fan et al., *Crit. Rev. Eukaryot. Gene Expr.* 14:183-202, 2004; Fiedler et al., *FASEB J.* 18:1120-2, 2004; Psyrri et al., *Cancer Res.,* 64:3079-86, 2004; Si et al., *J. Clin. Virol.* 32:19-23, 2004).

The association of HPV infection and cervical cancer has been the subject of considerable research and epidemiological study because of the high incidence of cervical cancer worldwide, estimated at 450,000 new cases per year. HPV types associated with a high risk of developing cervical cancer (HR-HPV) include HPV types 16, 18, 31, 33, 35, 39, 45, 51, 52, 56, 58, 59, 66, 68, and 73, although the epidemiological significance of individual types may vary with different geographical regions or clinical testing parameters (Munoz et al., *Int. J. Cancer* 111:278-85, 2004; Chaturvedi et al., *J. Med. Virol.* 75:105-13, 2005; Smith et al., *Int. J. Gynaecol. Obstet.* 87:131-7, 2004). HPV infections that are generally considered a low risk for developing into cervical cancer (LR-HPV) include HPV types 6, 11, 43, 43, 44, 61, 71, and 72.

In women infected with HPV, cervical infection may lead to condylomata (genital warts), cervical intraepithelial neoplasia (CIN), and cervical cancer (Kahn et al., *Adolesc. Med. Clin.* 15:301-21, ix, 2004). Cytological examination of cervical cells has been the primary screening tool for detecting cervical cancer in many countries, usually using the CIN grading system (1 to 3) to monitor precancerous lesions for determining treatment and/or further monitoring. In addition to cytological screening, molecular screening for HPV nucleic acid may be a cost-effective prognostic test that may allow extending the time interval between cytological tests (Wiley et al., *Curr. Oncol. Rep.* 6:497-506, 2004; Zielinski et al., *Obstet. Gynecol. Surv.* 59:543-53, 2004; Clavel et al., *Br. J. Cancer* 90:1803-8, 2004). Molecular assays have been developed for detection of selected HPV proteins and nucleic acid sequences in human biological specimens, e.g., Pap smears and biopsies (Chen et al., *Gynecol. Oncol.* 99:578-84, 2005; Carozzi et al., *Am. J. Clin. Pathol.* 124: 716-21, 2005; Molden et al., *Cancer Epidemiol. Biomarkers Prev.* 14:367-72, 2005; Asato et al., *J. Infect. Dis.* 189:1829-32, 2004; Federschneider et al., *Am. J. Obstet. Gynecol.* 191:757-61, 2004; Remmerbach et al., *J. Clin. Virol.* 30:302-8, 2004).

Vaccination against common HPV types may be useful to treat or prevent genital warts, or prevent development of cancers, particularly cervical cancers. Various forms of HPV vaccinations are available or are in development (Ault et al., *Vaccine* 22:3004-7, 2004; Corona Gutierrez et al., *Hum. Genet. Ther.* 15:421-31, 2004; Harper et al., *Lancet* 364: 1757-65, 2004; Roden et al., *Hum. Pathol.* 35:971-82, 2004).

There is a need to efficiently and sensitively detect the presence of HPV in biological specimens to provide diagnostic and prognostic information to physicians treating patients infected with HPV, particularly for women whose cervical tissue has been infected with HR-HPV types. There is also a need to efficiently and sensitively detect the presence of HPV in biological specimens obtained from individuals who have been vaccinated against HPV infection, to determine the short-term and long-term efficacy of the vaccination.

SUMMARY OF THE INVENTION

In one aspect, the present invention provides a combination of at least two oligomers for detecting a human papillomavirus type 33 (HPV33) target nucleic acid in a sample suspected of containing HPV33. Typically, the oligomer combination includes first and second amplification oligomers for specifically amplifying an HPV33 nucleic acid target region corresponding to the HPV33 E6 and/or E7 gene(s). In certain embodiments, (a) the first HPV33 amplification oligomer comprises a first target-hybridizing sequence that is from about 15 to about 27 contiguous nucleotides contained in the sequence of SEQ ID NO: 66 and that includes at least the sequence of SEQ ID NO: 67, SEQ ID NO: 68, or SEQ ID NO: 69; and (b) the second HPV33 amplification oligomer comprises a second target-hybridizing sequence that is from about 15 to about 27 contiguous nucleotides contained in the sequence of SEQ ID NO: 70 and that includes at least the sequence of SEQ ID NO: 71, SEQ ID NO: 72, or SEQ ID NO: 73. Particularly suitable first and second HPV33 amplification oligomers include (a) a first HPV33 amplification oligomer comprising a first target-hybridizing sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and (b) a second HPV33 amplification oligomer comprising a second target-hybridizing sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In typical variations, the oligomer combination is for detecting an HPV33 target nucleic acid in a sample suspected of containing HPV33 and at least one other HPV genotype (e.g., at least one of HPV types 16, 18, 31, 45, 52, and 58). In some variations the oligomer combination for detecting HPV 33 and at least one other HPV genotype includes a combination of oligomers substantially identical to two or more oligomers in Table 4.

In some preferred variations, the oligomer combination further includes first and second amplification oligomers for specifically amplifying an HPV type 31 (HPV31) nucleic acid target region corresponding to the HPV31 E6 and/or E7 gene(s). In some such embodiments, the first HPV31 amplification oligomer comprises a first target-hybridizing sequence that is from about 15 to about 27 contiguous nucleotides contained in the sequence of SEQ ID NO: 74 and that includes at least the sequence of SEQ ID NO: 75, SEQ ID NO: 76, or SEQ ID NO: 77; and the second HPV31 amplification oligomer comprises a second target-hybridizing sequence that is from about 15 to about 30 contiguous nucleotides contained in the sequence of SEQ ID NO: 78 and that includes at least the sequence of SEQ ID NO: 79, SEQ ID NO: 80, or SEQ ID NO: 81. Particularly suitable first and second HPV31 amplification oligomers include (a) a first HPV31 amplification oligomer comprising a first target-hybridizing sequence selected from SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and (b) a second HPV33 amplification oligomer comprising a second target-hybridizing sequence selected from SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some variations, the second HPV33 amplification oligomer is a promoter primer or promoter provider further comprising a promoter sequence located 5' to the target-hybridizing sequence. Similarly, in some embodiments further comprising HPV31 amplification oligomers, the second HPV31 amplification oligomer is a promoter primer or promoter provider further comprising a promoter sequence located 5' to the target-hybridizing sequence. Suitable promoter sequences include T7 RNA polymerase promoter sequences such as, e.g., the sequence shown in SEQ ID NO: 82. In more specific embodiments, the second HPV33 amplification oligomer has the sequence shown in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and/or the second HPV31 amplification oligomer has the sequence shown in SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

An oligomer combination may also include at least one capture probe oligomer. For example, the oligomer combination may further include an HPV33-specific capture probe oligomer and/or an HPV31-specific capture probe oligomer. Such HPV33- or HPV31-specific capture probe oligomers typically include a target-hybridizing sequence covalently attached to a sequence or moiety that binds to an immobilized probe. Suitable HPV33 and HPV31 target-hybridizing sequences are shown in SEQ ID NO: 50 and SEQ ID NO: 52, respectively. In particular variations, the HPV33 or HPV31 capture probe oligomer has a sequence as shown in SEQ ID NO: 51 or SEQ ID NO: 53, respectively.

In some embodiments, an oligomer combination further includes at least one HPV-33 specific and/or HPV31-specific detection probe oligomer. Suitable HPV33 detection probes include oligomers comprising a target-hybridizing sequence that is from about 14 to about 35 nucleotides in length and configured to specifically hybridize to a target sequence contained within SEQ ID NO: 83 from about nucleotide position 128 to about nucleotide position 164 (e.g., a target-hybridizing sequence selected from SEQ ID NO: 54, SEQ ID NO: 55, SEQ ID NO: 56, SEQ ID NO: 57, and SEQ ID NO: 58). Suitable HPV31 detection probes include oligomers comprising a target-hybridizing sequence that is from about 14 to about 40 nucleotides in length and configured to specifically hybridize to a target sequence contained within SEQ ID NO: 84 from about nucleotide position 675 to about nucleotide position 735 (e.g., a target-hybridizing sequence selected from SEQ ID NO: 59, SEQ ID NO: 60, SEQ ID NO: 61, SEQ ID NO: 62, SEQ ID NO: 63, SEQ ID NO: 64, and SEQ ID NO: 65).

In other aspects, the present invention provides a kit or a reaction mixture comprising an oligomer combination as above.

In yet another aspect, the present invention provides a method for detecting, in a sample, a human papillomavirus type 33 (HPV33) target nucleic acid (e.g., an HPV33 E6/E7 mRNA transcript). The method generally includes the following steps: (a) providing a sample suspected of containing HPV33; (b) contacting the sample with an oligomer combination for specifically amplifying an HPV33 nucleic acid target region, the oligomer combination comprising (i) a first HPV33 amplification oligomer comprising a first target-hybridizing sequence that is from about 15 to about 27 contiguous nucleotides contained in the sequence of SEQ ID NO: 66 and that includes at least the sequence of SEQ ID NO: 67, SEQ ID NO: 68, or SEQ ID NO: 69, and (ii) a second HPV33 amplification oligomer comprising a second target-hybridizing sequence that is from about 15 to about 27 contiguous nucleotides contained in the sequence of SEQ ID NO: 70 and that includes at least the sequence of SEQ ID NO: 71, SEQ ID NO: 72, or SEQ ID NO: 73; (c) performing an in vitro nucleic acid amplification reaction, where any HPV33 target nucleic acid present in said sample is used as a template for generating an HPV33 amplification product; and (d) detecting the presence or absence of the HPV33 amplification product, thereby indicating the presence or absence of HPV33 in the sample. Particularly suitable first and second type 33 amplification oligomers include (a) a first HPV33 amplification oligomer comprising a first target-hybridizing sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and (b) a second HPV33 amplification oligomer comprising a second target-hybridizing sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In typical variations of the method, the oligomer combination is for detecting an HPV33 target nucleic acid in a sample suspected of containing HPV33 and at least one other HPV genotype (e.g., at least one of HPV types 16, 18, 31, 45, 52, and 58). In some variations of the method, the sample is further tested for HPV 33 and at least one other HPV genotype, wherein two of more of the oligomers used in the method are substantially identical to those in Table 4.

In some preferred variations, the method is for further detecting in the sample an HPV type 31 (HPV31) target nucleic acid (e.g., an HPV31 E6/E7 mRNA transcript). In some such variations, the method further includes the following steps: (b') contacting the sample with an oligomer combination for specifically amplifying an HPV31 nucleic acid target region, the oligomer combination comprising (i) a first HPV31 amplification oligomer comprising a first target-hybridizing sequence that is from about 15 to about 27 contiguous nucleotides contained in the sequence of SEQ ID NO: 74 and that includes at least the sequence of SEQ ID NO: 75, SEQ ID NO: 76, or SEQ ID NO: 77, and (ii) a second HPV31 amplification oligomer comprising a second target-hybridizing sequence that is from about 15 to about 30 contiguous nucleotides contained in the sequence of SEQ ID NO: 78 and that includes at least the sequence of SEQ ID NO: 79, SEQ ID NO: 80, or SEQ ID NO: 81; (c') performing an in vitro nucleic acid amplification reaction, where any HPV31 target nucleic acid present in said sample is used as a template for generating an HPV31 amplification product; and (d') detecting the presence or absence of the HPV31 amplification product, thereby indicating the presence or absence of HPV31 in the sample.

In some embodiments of a method, the second HPV33 amplification oligomer is a promoter primer or promoter provider further comprising a promoter sequence located 5' to the target-hybridizing sequence. Similarly, in some embodiments further comprising detection of an HPV31 target nucleic acid, the second HPV31 amplification oligomer is a promoter primer or promoter provider further comprising a promoter sequence located 5' to the target-hybridizing sequence. Suitable promoter sequences include T7 RNA polymerase promoter sequences such as, e.g., the sequence shown in SEQ ID NO: 82. In more specific embodiments, the second HPV33 amplification oligomer has the sequence shown in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and/or the second HPV31 amplification oligomer has the sequence shown in SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

In certain variations of a method as above comprising detection of both HPV33 and HPV31 target nucleic acids, amplification step (c) is performed simultaneously with amplification step (c') in the same amplification reaction mixture. Typically, in such variations, detection step (d) is performed simultaneously with detection step (d') in the same detection reaction mixture.

Typically, the method for detecting the HPV33 target nucleic acid further includes purifying the HPV33 target nucleic acid from other components in the sample before step (b). In particular embodiments, the purifying step includes contacting the sample with at least one HPV33-specific capture probe oligomer comprising a target-hybridizing sequence covalently attached to a sequence or moiety that binds to an immobilized probe. A particularly suitable HPV33 target-hybridizing sequence is shown in SEQ ID NO: 50. In a more specific variation, an HPV33-specific capture probe oligomer has the sequence shown in SEQ ID NO: 51.

In variations of the method comprising detection of an HPV31 target nucleic acid, the method typically further includes purifying the HPV31 target nucleic acid from other components in the sample before step (b'). In particular embodiments, the purifying step includes contacting the sample with at least one HPV31-specific capture probe oligomer comprising a target-hybridizing sequence covalently attached to a sequence or moiety that binds to an immobilized probe. A particularly suitable HPV31 target-hybridizing sequence is shown in SEQ ID NO: 52. In a more specific variation, an HPV31-specific capture probe oligomer has the sequence shown in SEQ ID NO: 53.

In some embodiments, the detection step (d) includes contacting the amplification reaction of step (c) with an HPV33 detection probe oligomer configured to specifically hybridize to the HPV33 amplification product under conditions whereby the presence or absence of the HPV33 amplification product is determined, thereby indicating the presence or absence of HPV33 in the sample. In particular embodiments, the HPV33 detection probe includes a target-hybridizing sequence that is from about 14 to about 35 nucleotides in length and is configured to specifically hybridize to a target sequence contained within SEQ ID NO: 83 from about nucleotide position 128 to about nucleotide position 164. In specific variations, the HPV33 detection probe target-hybridizing sequence is selected from SEQ ID NO: 54, SEQ ID NO: 55, SEQ ID NO: 56, SEQ ID NO: 57, and SEQ ID NO: 58.

In some variations of the method comprising detection of an HPV 31 target nucleic acid, the detection step (d') includes contacting the amplification reaction of step (c') with an HPV31 detection probe oligomer configured to specifically hybridize to the HPV31 amplification product under conditions whereby the presence or absence of the HPV31 amplification product is determined, thereby indicating the presence or absence of HPV31 in the sample. In particular embodiments, the HPV31 detection probe includes a target-hybridizing sequence that is from about 14 to about 40 nucleotides in length and configured to specifically hybridize to a target sequence contained within SEQ ID NO: 84 from about nucleotide position 675 to about nucleotide position 735. In specific variations, the HPV31 detection probe target-hybridizing sequence is selected from SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments of a method utilizing a detection probe oligomer, the detection probe includes at least one label. In specific variations, the one or more label(s) are selected from a chemiluminescent label, a fluorescent label, a quencher, or any combination thereof.

In other embodiments of a method utilizing a detection probe oligomer, for detecting the HPV33 target nucleic acid, the detection step (d) occurs during the amplification step (c); and/or for detecting the HPV31 target nucleic acid, the detection (d') occurs during the amplification step (c'). In some such embodiments, the detection probe comprises a fluorescent label, a quencher, or both (e.g., a TaqMan detection probe or a molecular beacon).

In still other embodiments of a method utilizing a detection probe oligomer, the detection probe further comprises a non-target-hybridizing sequence. In particular embodiments, the detection probe comprising a non-target-hybridizing sequence is a hairpin detection probe such as, e.g., a molecular beacon or a molecular torch.

In certain embodiments of the method, the amplification reaction at step (c) and/or (c') is an isothermal amplification reaction or a PCR reaction. In specific variations, the isothermal amplification reaction is a transcription-mediated amplification (TMA) reaction (e.g., a reverse TMA reaction). In some embodiments of a method utilizing an isothermal or PCR amplification reaction, the reaction is a real-time amplification reaction.

In some preferred embodiments of the method, (i) the detection step (d) includes contacting the amplification reaction of step (c) with an HPV33 detection probe oligomer configured to specifically hybridize to the HPV33 amplification product under conditions whereby the presence or absence of the HPV33 amplification product is determined, thereby indicating the presence or absence of HPV33 in the sample; (ii) the detection step (d') includes contacting the amplification reaction of step (c') with an HPV31 detection probe oligomer configured to specifically hybridize to the HPV31 amplification product under conditions whereby the presence or absence of the HPV31 amplification product is determined, thereby indicating the presence or absence of HPV31 in the sample; (iii) step (c) is performed simultaneously with step (c') in the same amplification reaction mixture and step (d) is performed simultaneously with step (d') in the same detection reaction mixture; and (iv) the HPV33 and HPV31 detection probe oligomers are differentially labeled. In some such embodiments, each of the HPV33 and HPV31 detection probe oligomers comprises a label independently selected from a chemiluminescent label and a fluorescent label. In more particular variations, each of the HPV33 and HPV31 detection probe oligomers comprises a chemiluminescent label; in some such variations, the chemiluminescent labels for the HPV33 and HPV31 detection probe oligomers are characterized by different light emission kinetics sufficient to distinguish between HPV33-specific and HPV31-specific chemiluminescent signals. Suitable chemiluminescent labels for the HPV33 and HPV31 detection probe oligomers include labels comprising an acridinium ester (AE).

In still another aspect, the present invention provides a detection probe oligomer for detecting an HPV33 or HPV31 target nucleic acid. In some embodiments, a detection probe oligomer for detecting HPV33 comprises a target-hybridizing sequence that is from about 14 to about 35 nucleotides in length and configured to specifically hybridize to a target sequence contained within SEQ ID NO: 83 from about nucleotide position 128 to about nucleotide position 164 (e.g., a target-hybridizing sequence selected from SEQ ID NO: 54, SEQ ID NO: 55, SEQ ID NO: 56, SEQ ID NO: 57, and SEQ ID NO: 58). In some embodiments, a detection probe oligomer for detecting HPV31 comprises a target-hybridizing sequence that is from about 14 to about 40 nucleotides in length and configured to specifically hybridize to a target sequence contained within SEQ ID NO: 84 from about nucleotide position 675 to about nucleotide position 735 (e.g., a target-hybridizing sequence selected from SEQ ID NO: 59, SEQ ID NO: 60, SEQ ID NO: 61, SEQ ID NO: 62, SEQ ID NO: 63, SEQ ID NO: 64, and SEQ ID NO: 65).

In some embodiments of a detection probe oligomer, the detection probe includes at least one label. In specific variations, the one or more label(s) are selected from a chemiluminescent label, a fluorescent label, a quencher, or any combination thereof. In more specific variations, the detection probe comprises a fluorescent label and a quencher (e.g., a TaqMan detection probe or a molecular beacon).

In other embodiments of a detection probe oligomer, the detection probe further comprises a non-target-hybridizing sequence. In particular variations, the detection probe comprising a non-target-hybridizing sequence is a hairpin detection probe such as, e.g., a molecular beacon or a molecular torch.

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" or "biological sample" refers to any tissue or material derived from a living or dead human that may contain a human papillomavirus (HPV) target nucleic acid, including, e.g., samples of larynx, oral cavity, oropharynx, tonsil, or esophagus tissue, respiratory tissue or exudates, cervical or anal swab samples, biopsy tissue including lymph nodes, gastrointestinal tissue, feces, urine, semen, sputum, peripheral blood, plasma, serum or other body fluids, tissues or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support. Samples may further include cross-linked tissues or material derived from a human, such as samples that are contained in a media such as BD SurePath Preservative Fluid (Becton, Dickinson and Company, Franklin Lakes, N.J.), or formalin-fixed paraffin-embedded samples. Samples may further include tissues or material derived from a human and are suspended in a Cytology media such as ThinPrep Cytology Reagent (Hologic, Inc., Bedford, Mass.).

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality of strains within a species. It is understood that other reasons exist for configuring a target-hybridizing sequence to have less than 100% complementarity to a target nucleic acid.

Oligomer target-hybridizing sequences defined herein by reference to a specific sequence (e.g., by reference a region within SEQ ID NO: 83 or SEQ ID NO: 84) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences. Similarly, and again by way of example, where a target-hybridizing sequence for a detection probe oligomer is defined reference to a specific sequence, it is understood that the detection probe may include a corresponding detection probe oligomer having a target-hybridizing sequence that is the complement of the specific reference sequence; or where a detection probe oligomer is defined by its configuration to hybridize to a specific sequence, it is understood that the detection probe may include a corresponding detection probe oligomer having a target-hybridizing sequence that is configured to hybridize to the complement of the specific reference sequence.

The term "target a sequence," as used herein in reference to a region of an HPV nucleic acid, refers to a process whereby an oligonucleotide hybridizes to the target sequence in a manner that allows for amplification and detection as described herein. In one preferred embodiment, the oligonucleotide is complementary with the targeted HPV nucleic acid sequence and contains no mismatches. In another preferred embodiment, the oligonucleotide is complementary but contains 1, 2, 3, 4, or 5 mismatches with the targeted HPV nucleic acid sequence. Preferably, the oligonucleotide that hybridizes to the HPV nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced HPV target region. Such an oligonucleotide is not limited to targeting that sequence only, but is rather useful as a composition, in a kit or in a method for targeting an HPV target nucleic acid. The oligonucleotide is designed to function as a component of an assay for amplification and detection of HPV from a sample, and therefore is designed to target HPV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the amplification oligonucleotide target-hybridizing sequence.

The term "fragment," as used herein in reference to an HPV target nucleic acid, refers to a piece of contiguous nucleic acid, wherein the number of contiguous nucleotides in the fragment are less than that for the entire target nucleic acid.

The term "region," as used herein, refers to a portion of a nucleic acid wherein said portion is smaller than the entire nucleic acid. For example, when the nucleic acid in reference is an oligonucleotide promoter primer, the term "region" may be used to refer to the smaller promoter portion of the entire oligonucleotide. Similarly, and also as example only, when the nucleic acid is an HPV E6 and/or E7 segment of an HPV genome (e.g., an E6/E7 mRNA transcript), the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectable moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 15-27 contiguous nucleotides in length includes 15, 16, 17, 18, 19, 20, 21, 22, 23, 24, 25, 26, and 27).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

A "terminating oligonucleotide" is an oligonucleotide comprising a base sequence that is substantially complementary to a sequence within the target nucleic acid in the vicinity of the 5'-end of the target region, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., *Nucleic Acids Res.* 26:2224-9, 1988, incorporated by reference herein.) Other modifications as described elsewhere herein may be utilized in addition to or in place of 2'-O-ME ribonucleotides. For example, a terminating oligonucleotide may comprise PNA or an LNA. (See, e.g., Petersen et al., *J. Mol. Recognit.* 13:44-53, 2000, incorporated by reference herein.) A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. While a terminating oligonucleotide typically or necessarily includes a 3'-blocking moiety, "3'-blocked" oligonucleotides are not necessarily terminating oligonucleotides.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription associated amplification method are embodiments of amplification methods used for detection of HPV target sequences as described herein. Variations of transcription-associated amplification are well known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual,* $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual,* $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of HPV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

BRIEF DESCRIPTION OF THE DRAWINGS

FIG. 1 illustrates a reference sequence for the E6/E7 region of the HPV type 33 genome (SEQ ID NO: 83)

FIG. 2 illustrates a reference sequence for the E6/E7 region of the HPV type 31 genome (SEQ ID NO: 84).

DETAILED DESCRIPTION OF THE INVENTION

The present invention provides compositions, kits and methods for amplifying and detecting human papillomavirus (HPV) nucleic acid from a sample, specifically sequences corresponding to the E6/E7 region of the HPV type 33 (HPV33) and/or HPV type 31 (HPV31) genome. The compositions, kits and methods provide oligonucleotide sequences that recognize target sequences within the HPV33 or HPV31 E6/E7 region or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as capture probe oligomers for capturing and separating target nucleic acids from various sample components. Other oligonucleotides may be used as probes for detecting amplified sequences of HPV33 or HPV31.

The methods provide for the sensitive and specific detection of HPV33 and/or HPV31 nucleic acids, such as, e.g., HPV33 and/or HPV31 E6/E7 mRNA transcripts. The methods include performing a nucleic acid amplification of HPV33 and/or HPV31 sequences and detecting the amplified product by, for example, specifically hybridizing the amplified product with a nucleic acid detection probe that provides a signal to indicate the presence of HPV33 or HPV31 in the sample. The amplification step includes contacting the sample with one or more amplification oligomers specific for a target sequence in the HPV33 or HPV31 E6/E7 region to produce an amplified product if HPV33 or HPV31 nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

Preferred compositions of the instant invention are configured to specifically hybridize to an E6/E7 nucleic acid target region of HPV33 or HPV31 with minimal cross-reactivity to other nucleic acids suspected of being in a sample. In some aspects, the compositions of the instant invention are configured to specifically hybridize to an E6/E7 nucleic acid target region of HPV33 or HPV31 with minimal cross-reactivity to one or more other HPV types. For example, in certain embodiments, compositions of the invention are configured to specifically hybridize to an E6/E7 region of HPV33 with minimal cross-reactivity to one or more of HPV types 16, 18, 31, 35, 39, 45, 51, 52, 56, 58, 59, and 68; in some such variations, the compositions are configured to specifically hybridize to an E6/E7 region of HPV33 with minimal cross-reactivity to at least (i) HPV31 and/or (ii) one or both of closely related HPV types 52 and 58 (e.g., with minimal cross-reactivity to each of HPV types 31, 52, and 58). In other embodiments, compositions of the invention are configure to specifically hybridize to an E6/E7 region of HPV31 with minimal cross-reactivity to one or more of HPV types 16, 18, 33, 35, 39, 45, 51, 52, 56, 58, 59, and 68; in some such variations, the compositions are configured to specifically hybridize to an E6/E7 region of HPV31 with minimal cross-reactivity to at least (i) HPV33 and/or (ii) one or both of closely related HPV types 52 and 58 (e.g., with minimal cross-reactivity to each of HPV types 33, 52, and 58). In one aspect, the compositions of the instant invention are part of a multiplex system that further includes components and methods for detecting one or more of these HPV types (e.g., a multiplex system for detecting one or more of HPV33 and HPV31).

In certain aspects of the invention, a combination of at least two oligomers is provided for the detection of an HPV33 target nucleic acid in a sample suspected of containing HPV33. Typically, the oligomer combination includes first and second amplification oligomers for specifically amplifying an HPV33 nucleic acid target region corresponding to the HPV33 E6 and/or E7 gene(s). In certain embodiments, (a) the first HPV33 amplification oligomer comprises a first target-hybridizing sequence that is from about 15 to about 27 contiguous nucleotides in length and substantially corresponding to, or identical to, a sequence that is contained in the sequence of SEQ ID NO: 66 and that includes at least the sequence of SEQ ID NO: 67, SEQ ID NO: 68, or SEQ ID NO: 69; and (b) the second HPV33 amplification oligomer comprises a second target-hybridizing sequence that is from about 15 to about 27 contiguous nucleotides in length and substantially corresponding to, or identical to, a sequence that is contained in the sequence of SEQ ID NO: 70 and that includes at least the sequence of SEQ ID NO: 71, SEQ ID NO: 72, or SEQ ID NO: 73. In some embodiments of the oligomer combination, (a) the first HPV33 amplification oligomer comprises a first target-hybridizing sequence substantially corresponding to, or identical to, a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and/or (b) the second HPV33 amplification oligomer comprises a second target-hybridizing sequence substantially corresponding to, or identical to, a sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In typical variations, the oligomer combination is for detecting an HPV33 target nucleic acid in a sample suspected of containing HPV33 and at least one other HPV genotype (e.g., at least one of HPV types 16, 18, 31, 45, 52, and 58). In one variation, the combination of oligomers is a combination that includes at least two oligomers that are substantially identical to oligomers in Table 4.

In some preferred variations, the oligomer combination further includes first and second amplification oligomers for specifically amplifying an HPV type 31 (HPV31) nucleic acid target region corresponding to the HPV31 E6 and/or E7 gene(s). In certain embodiments, (a) the first HPV31 amplification oligomer comprises a first target-hybridizing sequence that is from about 15 to about 27 contiguous nucleotides in length and substantially corresponding to, or identical to, a sequence that is contained in the sequence of SEQ ID NO: 74 and that includes at least the sequence of SEQ ID NO: 75, SEQ ID NO: 76, or SEQ ID NO: 77; and (b) the second HPV31 amplification oligomer comprises a second target-hybridizing sequence that is from about 15 to about 30 contiguous nucleotides in length and substantially corresponding to, or identical to, a sequence that is contained in the sequence of SEQ ID NO: 78 and that includes at least the sequence of SEQ ID NO: 79, SEQ ID NO: 80, or SEQ ID NO: 81. In some embodiments of the oligomer combination, (a) a first HPV31 amplification oligomer comprising a first target-hybridizing sequence substantially corresponding to, or identical to, a sequence selected from SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33; and/or (b) a second HPV31 amplification oligomer comprising a second target-hybridizing sequence substantially corresponding to, or identical to, a sequence selected from SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In certain embodiments, an amplification oligomer as described herein is a promoter primer or promoter provider further comprising a promoter sequence located 5' to the target-hybridizing sequence and which is non-complementary to the HPV33 or HPV31 target nucleic acid. For example, in some embodiments of an oligomer combination as described herein for amplification of a HPV33 or HPV31 target region, the second amplification oligomer is a promoter primer or promoter provider further comprising a 5' promoter sequence. In particular embodiments, the promoter sequence is a T7 RNA polymerase promoter sequence such as, for example, a T7 promoter sequence having the sequence shown in SEQ ID NO: 82. In specific variations, the second HPV33 amplification oligomer is a promoter primer or promoter provider having the sequence shown in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and/or the second HPV31 amplification oligomer is a promoter primer or promoter provider having the sequence shown in SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

In some embodiments, an oligomer combination as described herein further includes a terminating oligonucleotide (also referred to herein as a "blocker" oligonucleotide) comprising comprises a base sequence substantially complementary (e.g., fully complementary) to a sequence contained within the target nucleic acid in the vicinity of the 5'-end of the target region. A terminating oligomer is typically used in combination with, e.g., a promoter provider amplification oligomer, such as, for example, in certain embodiments described herein relating to transcription-mediated amplification (TMA).

In some embodiments, an oligomer combination as described herein further comprises at least one capture probe oligomer for capture of an HPV33 and/or HPV31 target nucleic acid. Such capture probes may be specific for either HPV33 or HPV31 target nucleic acid. In some embodiments, the capture probe oligomer comprises a target-hybridizing sequence substantially corresponding to a sequence contained in the complement of SEQ ID NO: 83 (representative HPV33 E6/E7 region) or SEQ ID NO: 84 (representative HPV31 E6/E7 region), wherein the target-hybridizing sequence is covalently attached to a sequence or moiety that binds to an immobilized probe. In specific variations, the target-hybridizing sequence of an HPV33-specific capture probe oligomer comprises or consists of a sequence substantially corresponding to, or identical to, SEQ ID NO: 50; and/or the target hybridizing sequence of an HPV31-specific capture probe oligomer comprises or consists of a sequence substantially corresponding to, or identical to, SEQ ID NO: 52. Particularly suitable HPV33 or HPV31 capture probe oligomers for use in accordance with the present invention comprise or consist of a sequence as shown in SEQ ID NO: 51 or SEQ ID NO: 53, respectively.

In certain variations, an oligomer combination as described herein further comprises at least one detection probe oligomer configured to specifically hybridize to an HPV33 or HPV31 target sequence that is amplifiable using the first and second HPV33 or HPV31 amplification oligomers (e.g., an HPV target sequence that is flanked by the target-hybridizing sequences of the first and second amplification oligomers). Suitable HPV33 detection probes include oligomers comprising a target-hybridizing sequence that is from about 14 to about 35 nucleotides in length and configured to specifically hybridize to a target sequence contained within SEQ ID NO: 83 from about nucleotide position 128 to about nucleotide position 164. For example, in some variations, an HPV33 detection probe comprises a target-hybridizing sequence substantially corresponding to, or identical to, a sequence selected from SEQ ID NO: 54, SEQ ID NO: 55, SEQ ID NO: 56, SEQ ID NO: 57, and SEQ ID NO: 58. Suitable HPV31 detection probes include oligomers comprising a target-hybridizing sequence that is from about 14 to about 40 nucleotides in length and configured to specifically hybridize to a target sequence contained within SEQ ID NO: 84 from about nucleotide position 675 to about nucleotide position 735. For example, in some variations, an HPV31 detection probe comprises a target-hybridizing sequence substantially corresponding to, or identical to, a sequence selected from SEQ ID NO: 59, SEQ ID NO: 60, SEQ ID NO: 61, SEQ ID NO: 62, SEQ ID NO: 63, SEQ ID NO: 64, and SEQ ID NO: 65.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. No. 5,118,801 and U.S. Pat. No. 5,312,728, supra). Methods for using such hairpin probes are well known in the art.

In yet other embodiments, a detection probe is a linear oligomer that does not substantially form conformations held by intramolecular bonds. In specific variations, a linear detection probe oligomer includes a chemiluminescent compound as the label, preferably an acridinium ester (AE) compound.

Also provided by the present invention are detection probe oligomers and capture probe oligomers as described herein.

In another aspect, the present invention provides methods for detecting an HPV33 target nucleic acid and/or HPV31 target nucleic acid in a sample using an oligomer combination as described herein. In certain embodiments, a method for detecting an HPV33 target nucleic acid in a sample suspected of containing HPV33 generally includes the following steps: (b) contacting the sample with an oligomer combination for specifically amplifying an HPV33 nucleic acid target region, where the oligomer combination includes first and second HPV33 amplification oligomers as described above; (c) performing an in vitro nucleic acid amplification reaction, where any HPV33 target nucleic acid present in said sample is used as a template for generating an HPV33 amplification product; and (d) detecting the presence or absence of the HPV33 amplification product, thereby indicating the presence or absence of HPV33 in the sample. In some embodiments, the sample is further suspected of containing at least one other HPV type (e.g., at least one of HPV types 16, 18, 31, 35, 39, 45, 51, 52, 56, 58, 59, and 68; typically at least one of HPV types 31, 52, and 58), where the method specifically detects the presence or absence of HPV33 irrespective of the presence of the other HPV type(s) (e.g., the method is capable of distinguishing HPV33 from the other HPV types, such as at least one of HPV types 16, 18, 31, 35, 39, 45, 51, 52, 56, 58, 59, and 68; typically at least one of HPV types 31, 52, and 58.)

In some variations, a method detecting an HPV31 target nucleic acid in a sample suspected of containing HPV31 generally includes the following steps. (b') contacting the sample with oligomer combination for specifically amplifying an HPV31 nucleic acid target region, where the oligomer combination includes first and second HPV31 amplification oligomers as described above; (c') performing an in vitro nucleic acid amplification reaction, where any HPV31 target nucleic acid present in said sample is used as a template for generating an HPV31 amplification product; and (d') detecting the presence or absence of the HPV31 amplification product, thereby indicating the presence or absence of HPV31 in the sample. In some embodiments, the sample is further suspected of containing at least one other HPV type (e.g., at least one of HPV types 16, 18, 33, 35, 39, 45, 51, 52, 56, 58, 59, and 68; typically at least one of HPV types 33, 52, and 58), where the method specifically detects the presence or absence of HPV31 irrespective of the presence of the other HPV type(s) (e.g., the method is capable of distinguishing HPV31 from the other HPV types, such as at least one of HPV types 16, 18, 31, 35, 39, 45, 51, 52, 56, 58, 59, and 68; typically at least one of HPV types 33, 52, and 58.)

In some preferred embodiments, a detection method as above is for detecting both HPV33 and HPV31 in a sample suspected of containing at least one of HPV33 and HPV31. In some such embodiments, the method includes (I) steps (b)-(d) as above for detection of HPV33 and (II) steps (b')-(d') above for detecting HPV31. Any one or more of the steps for detecting HPV33 and HPV31 may be performed separately or together. In some variations, any one or more of steps (b)-(d) for HPV33 detection are performed together with the one or more corresponding steps (b')-(d') for HPV31 detection in the same reaction mixture (e.g., amplification step (c) may be performed with during amplification step (c') in the same reaction mixture; and/or detection step (d) may be performed with detection step (d') in the same reaction mixture). Accordingly, in some embodiments, the method for detecting HPV33 and HPV31 is performed as a multiplex assay for simultaneous detection of both HPV33 and HP31 within the same reaction mixture.

A detection method in accordance with the present invention typically further includes the step of (a) providing the sample suspected of containing HPV33 and/or HPV31. In certain embodiments, "providing" a sample to be used in steps (b)-(d) and/or steps (b')-(d') includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the HPV33 and/or HPV31 target nucleic acid from other components in the sample before the contacting step. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HPV nucleic acid and other sample components.

In some embodiments, an HPV33 or HPV31 nucleic acid is selectively separated from other sample components by specifically hybridizing the HPV target nucleic acid to a capture probe oligomer. The capture probe oligomer comprises a target-hybridizing sequence configured to specifically hybridize to an HPV target sequence so as to form a target-sequence:capture-probe complex that is separated from sample components. Suitable HPV33 and HPV31 target-hybridizing sequences are shown in SEQ ID NO: 50 and SEQ ID NO: 52, respectively. In a preferred variation, the specific target capture binds the HPV target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds the capture probe, with its bound target sequence, to an immobilized probe attached to a solid support, thereby permitting the hybridized target nucleic acid to be separated from other sample components. In embodiments comprising amplification and detection of both HPV33 and HPV31, selective separation of HPV33 and HPV31 nucleic acids may be performed simultaneously from a single sample.

In more specific embodiments, the capture probe oligomer includes a tail portion (e.g., a 3' tail) that is not complementary to the HPV target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the HPV33 or HPV31 capture probe oligomer has a sequence as shown in SEQ ID NO: 51 or SEQ ID NO: 53, respectively.

Target capture typically occurs in a solution phase mixture that contains one or more capture probe oligomers that hybridize specifically to the HPV target sequence under hybridizing conditions, usually at a temperature higher than the $T_m$ of the tail-sequence:immobilized-probe-sequence duplex. For embodiments comprising a capture probe tail, the HPV-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:HPV-target-sequence may be washed one or more times to further remove other sample components. Preferred embodiments use a particulate solid support, such as paramagnetic beads, so that particles with the attached HPV-target:capture-probe:immobilized-probe complex may be suspended in a washing solution and retrieved from the washing solution, preferably by using magnetic attraction. To limit the number of handling steps, the HPV target nucleic acid may be amplified by simply mixing the HPV target sequence in the complex on the support with amplification oligomers and proceeding with amplification steps.

Amplifying an HPV33 or HPV31 target sequence utilizes an in vitro amplification reaction using at least two amplification oligomers that flank a target region to be amplified. In particular embodiments, the HPV33 target region to be amplified substantially corresponds to SEQ ID NO: 83 from about nucleotide position 128 to about nucleotide position 164. In particular embodiments, the HPV31 target region to be amplified substantially corresponds to SEQ ID NO: 84 from about nucleotide position 675 to about nucleotide position 735. Particularly suitable amplification oligomer combinations for amplification of these target regions are described herein. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art and are readily used in accordance with the methods of the present invention.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. For example, if the target nucleic acid is the E6/E7 region of the HPV33 genome or an RNA corresponding to the E6/E7 region, the amplified product will contain a target sequence in or complementary to a sequence in E6/E7 region, and a probe will bind directly or indirectly to a sequence contained in the amplified product to indicate the presence of the target nucleic acid in the tested sample.

Preferred embodiments of detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified HPV sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein. In some preferred embodiments of the method for detecting HPV sequences, such as in certain embodiments using transcription-mediated amplification (TMA), the detection probe is a linear chemiluminescently labeled probe, more preferably, a linear acridinium ester (AE) labeled probe.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

Examples of oligomers that are typically blocked at the 3' end—and which are particularly suitable in certain embodiments using transcription-mediated amplification—are promoter providers. As described previously, a promoter provider comprises first target-hybridizing region and, situated 5' to the first region, a second region comprising a promoter sequence for an RNA polymerase. The promoter provider oligonucleotide is modified to prevent the initiation of DNA synthesis from its 3'-terminus, such as by including a blocker group as discussed above. In some embodiments, a promoter provider for use in accordance with an HPV33 detection method comprises a target-hybridizing sequence substantially corresponding to, or identical to, a sequence that is contained in the sequence of SEQ ID NO: 70 and that includes at least the sequence of SEQ ID NO: 71, SEQ ID NO: 72, or SEQ ID NO: 73 (for example, a target-hybridizing sequence having a sequence substantially corresponding to, or identical to, a sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16; e.g., an HPV33 promoter provider may have a sequence as shown in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24). In some embodiments, a promoter provider for use in accordance with an HPV31 detection method comprises a target-hybridizing sequence substantially corresponding to, or identical to, a sequence that is contained in the sequence of SEQ ID NO: 78 and that includes at least the sequence of SEQ ID NO: 79, SEQ ID NO: 80, or SEQ ID NO: 81 (for example, a target-hybridizing sequence having a sequence substantially corresponding to, or identical to, a sequence selected from SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41; e.g., an HPV31 promoter provider may have a sequence as shown in SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49).

Another example of typically 3'-blocked oligomers are terminating ("blocker") oligonucleotides, previously described above. A terminating oligomer is typically used in combination with, e.g., a promoter provider amplification oligomer, such as, for example, in certain embodiments described herein relating to transcription-mediated amplification (TMA). A terminating oligomer hybridizes to a sequence contained within the target nucleic acid in the vicinity of the 5'-end of the target region so as to "terminate" primer extension of a nascent nucleic acid that includes a priming oligonucleotide, thereby providing a defined 3'-end for the nascent nucleic acid strand.

Other embodiments using transcription-mediated amplification utilize a promoter primer, which comprises a first target-hybridizing region and, situated 5' to the first region, a second region comprising a promoter sequence for an RNA polymerase, but which is not modified to prevent the initiation of DNA synthesis from its 3'-terminus. In certain variations, a promoter primer for use in accordance with an HPV33 detection method comprises a target-hybridizing sequence substantially corresponding to, or identical to, a sequence that is contained in the sequence of SEQ ID NO: 70 and that includes at least the sequence of SEQ ID NO: 71, SEQ ID NO: 72, or SEQ ID NO: 73 (for example, a target-hybridizing sequence having a sequence substantially corresponding to, or identical to, a sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16; e.g., an HPV33 promoter primer may have a sequence as shown in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24). In certain variations, a promoter primer for use in accordance with an HPV31 detection method comprises a target-hybridizing sequence substantially corresponding to, or identical to, a sequence that is contained in the sequence of SEQ ID NO: 78 and that includes at least the sequence of SEQ ID NO: 79, SEQ ID NO: 80, or SEQ ID NO: 81 (for example, a target-hybridizing sequence having a sequence substantially corresponding to, or identical to, a sequence selected from SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41; e.g., an HPV31 promoter primer may have a sequence as shown in SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49).

Assays for detection of an HPV target nucleic acid may optionally include a non-target internal control (IC) nucleic acid that is amplified and detected in the same assay reaction mixtures by using amplification and detection oligomers specific for the IC sequence. IC nucleic acid sequences can be synthetic nucleic acid sequences that are spiked into a sample or the IC nucleic acid sequences may be a cellular component. IC nucleic acid sequences that are cellular components can be from exogenous cellular sources or endogenous cellular sources relative to the specimen. An exogenous cellular source, for example, is a cell that is added into the sample and that then flows through the sample processing procedures along with the specimen. A more particular example would be the addition of a HeLa cell, Jurkat cell, SiHa cell or other to the sample medium along with the specimen that is collected for testing (e.g., a vaginal swab specimen). The specimen and the exogenous cells are then processed, amplified and detected, the specimen being amplified and detected using amplification and detection oligomers for identifying the target sequence of interest and the exogenous cells being amplified and detected using amplification and detection oligomers for identifying an IC target sequence. An endogenous cellular source is a cellular source that would naturally be obtained when gathering the specimen. One example: epithelial cells will present when obtaining a specimen via a vaginal swab. Similar then to the above exemplary exogenous cells process described, the specimen and the endogenous cellular source are both processed, amplified, and detected. The specimen being amplified and detected using amplification and detection oligomers for identifying the target sequence of interest and the endogenous cells being amplified and detected using amplification and detection oligomers for identifying an IC target sequence; typically a housekeeping gene present in the endogenous cellular source, such as a beta-globulin gene. (See e.g., Poljak et al., J. Clin. Virol, 25: S89-97, 2002; U.S. Pat. No. 6,410,321; and US Patent Application Publication No. 2004-0023288; each incorporated by reference herein). Use of a cellular source IC allows for a control from sample collection through detection. Synthetic nucleic acid sequences provide for control of amplification and detection.

In certain embodiments, amplification and detection of a signal from the amplified IC sequence demonstrates that the assay reagents, conditions, and performance of assay steps were properly used in the assay if no signal is obtained for the intended target HPV nucleic acid (e.g., samples that test negative for the HPV33 and/or HPV31 target nucleic acid). An IC may also be used as an internal calibrator for the assay when a quantitative result is desired, i.e., the signal obtained from the IC amplification and detection is used to set a parameter used in an algorithm for quantitating the amount of HPV nucleic acid in a sample based on the signal obtained for an amplified HPV target sequence. ICs are also useful for monitoring the integrity of one or more steps in an assay. A preferred embodiment of a synthetic IC nucleic acid sequence is a randomized sequence that has been derived from a naturally occurring source (e.g., an HIV sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The amplification oligomers and probe for the IC target sequence are configured and synthesized by using any well-known method provided that the amplification oligomers and probe function for amplification of the IC target sequence and detection of the amplified IC sequence using substantially the same assay conditions used to amplify and detect the HPV target sequence. In preferred embodiments that include a target capture-based purification step, it is preferred that a target capture probe specific for the IC target be included in the assay in the target capture step so that the IC is treated in the assay in a manner analogous to that for the intended HPV analyte in all of the assay steps.

In some preferred embodiments, the detection of HPV33 and HPV31 is performed as a multiplex assay. Typically, in such embodiments, the amplification of an HPV33 target nucleic acid is performed simultaneously with the amplification of an HPV31 target nucleic acid in the same amplification reaction mixture, and the detection of the HPV33 amplification product is performed simultaneously with the detection of the HPV31 amplification product in the same detection reaction mixture. The detection of HPV33 and HPV31 typically includes contacting the amplification reaction with differentially labeled HPV33 and HPV31 detection probe oligomers configured to specifically hybridize to the HPV33 and HPV31 amplification products under conditions whereby the presence or absence of the HPV33 and HPV31 amplification products is determined. In some such variations, each of the HPV33 and HPV31 detection probe oligomers comprises either a chemiluminescent label or a fluorescent label. For example, each of the HPV33 and HPV31 detection probe oligomers may comprise a different chemiluminescent label, such as, e.g., chemiluminescent labels characterized by different light emission kinetics sufficient to distinguish between HPV33-specific and HPV31-specific chemiluminescent signals. Suitable chemiluminescent labels for the HPV33 and HPV31 detection probe oligomers include acridinium ester (AE) labels with differential light kinetics. In particular variations, one detection probe oligomer (e.g., a probe specific for an HPV33 amplification product) comprises an 2' methyl acridinium ester label (also referred to as a "glower" probe), while a second detection probe oligomer (e.g., a probe specific for an HPV31 amplification product) comprises an ortho fluoro acridinium ester label (also referred to herein has a "flasher" probe), the flasher probe exhibiting more rapid light-off kinetics than the glower probe. An ETF algorithm may be used to deconvolute light-off kinetics and calculate each signal. If using an internal control (IC), the IC probe may also, e.g., be a flasher probe, which can be distinguished from the HPV test flasher signal by, for example, using a much lower probe input than for the HPV flasher probe. (See e.g., U.S. Pub. No. 2012/0003646).

Also provided by the subject invention is a reaction mixture for amplification and/or detection of an HPV33 and/or HPV31 target nucleic acid. A reaction mixture in accordance with the present invention at least comprises one or more of the following: an oligomer combination as described herein for amplification of an HPV33 and/or HPV31 target nucleic acid; a capture probe oligomer as described herein for purifying the HPV33 and/or HPV31 target nucleic acid; and a detection probe oligomer as described herein for determining the presence or absence of an HPV33 and/or HPV31 amplification product. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an HPV33 and/or HPV31 target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an amplification oligomer combination as described herein for amplification of an HPV33 and/or HPV31 target nucleic acid; a capture probe oligomer as described herein for purifying the HPV33 and/or HPV31 target nucleic acid; and a detection probe oligomer as described herein for determining the presence or absence of an HPV33 and/or HPV31 amplification product. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region of an HPV genome, or it may include amplification oligomers for multiple HPV target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

EXAMPLE 1

HPV 31/33 Genotyping Assay

This example describes an exemplary HPV 31/33 genotyping assay in accordance with the present invention. The assay of this example is also referred to herein as the "APTIMA HPV 31/33 genotyping assay" or "APTIMA 31/33 GT assay."

Table 1 below lists all the oligomers used in this assay at their respective concentrations.

TABLE 1

Oligomers used in HPV 31/33 genotyping assay

| Oligo description | Oligo SEQ ID NO | Concentration |
| --- | --- | --- |
| HPV31 target capture oligo | 53 | 0.9 pmol/rxn |
| HPV33 target capture oligo | 51 | 0.7 pmol/rxn |
| HPV31 T7 amp oligo | 42 | 6.6 pmol/rxn |
| HPV33 T7 amp oligo | 20 | 5 pmol/rxn |
| HPV31 non-T7 amp oligo | 29 | 6.7 pmol/rxn |
| HPV33 non-T7 amp oligo | 5 | 6.6 pmol/rxn |
| HPV33 detection probe | 54 | $1.3 \times 10^6$ RLU/ml |
| HPV31 detection probe | 59 | $8.5 \times 10^6$ RLU/ml |

This assay utilized methods and reagents from the APTIMA® HPV assay (see e.g., APTIMA HPV Assay, Cat. No. 303012, Gen-Probe Incorporated, San Diego, Calif.). Generally, the testing was performed using a DTS 402 instrument system and various APTIMA reagents according to the APTIMA assay package insert. A target capture reaction mixture was prepared to contain target capture oligos SEQ ID NO53 and SEQ ID NO: 51, which are configured to specifically hybridize HPV31 and HPV33 target nucleic acids, respectively. An amplification reaction mixture was prepared to contain SEQ ID NOS: 5, 20, 29 and 42 as amplification oligomers. The detection reaction mixture was prepared to contain SEQ ID NOS: 54 and 59 as AE labeled detection probe oligomers configured to specifically hybridize amplification product generated from HPV31 and HPV 33, respectively.

Capture, amplification and detection reactions were performed as multiplex reactions. HPV positive samples included HPV negative ThinPrep liquic pap samples spiked with various concentrations of HPV31 in vitro transcripts (IVT), with HPV33 IVT, or with HPV31 and HPV33 IVT; and HPV positive samples. Negative control sample were HPV negative ThinPrep liquic pap samples without any HPV IVT spiked therein. HPV positive or HPV negative was determined using the APTIMA® HPV assay (cat no. 303012, Gen-Probe Incorporated). Samples were diluted with sample transport media (STM) at a ratio of 1:2.9, and then a target capture reaction was performed. Reaction mixtures were incubated for 35 minutes at 62° C., followed by 30 minutes at room temperature. The Gen-Probe SB100 system was used for all incubation steps. A capture and wash step was performed using magnetic beads and the Gen-Probe Target Capture System (cat no. 104555, Gen-Probe Incorporated). Following target capture, the amplification reaction mixture and oil was added to each reaction tube and incubated for 10 minutes at 62° C. for primer anneal. Following the 10 minute incubation, enzyme reagent was added to each reaction mixture and the reactions were incubated for 60 minutes at 42° C. to allow for nucleic acid amplification of target nucleic acids. Following amplification a detection reaction mixture was added to each amplification reaction and incubated for 20 minutes at 62° C. to allow for probe to hybridize to amplification product in the reactions. A selection reagent was added to the reaction tube and incubated for 10 minutes at 62° C. followed by cooling at room temperature. Detection of target was performed using the Gen-Probe Luminometer with Auto Detect 1 and Auto Detect 2 reagents. Detection of amplification products was measured in Relative Light Units (RLU). In general, for determining presence of target, an RLU cutoff value of 200,000 RLU was used for HPV31 and 800,000 RLU was used for HPV33

Analytical Sensitivity and Specificity

Very good analytical sensitivity was observed for both HPV types 31 and 33 for IVT spiked into negative clinical samples. 100% positivity was obtained for both HPV types at concentrations as low as 10 copies/reaction.

Analytical sensitivity at also analyzed for both targets in the presence of the other target. HPV31 IVT and HPV33 IVT were detected at 30 copies per reaction in the presence of 1,000,000 copies per reaction of each of HPV types 6, 11, 16, 18, 35, 39, 42, 43, 44, 45, 51, 52, 53, 56, 58, 59, 61, 66, 68, 71, and 81, and the results showed that both HPV31 and HPV33 targets were efficiently amplified in the presence of these other targets without cross-reactivity.

Cross-reactivity was further analyzed. Negative clinical pools were spiked with 1,000,000 copies per reaction of either HPV 52, HPV58 or both HPV52 and HPV58. HPV 31 and HPV33 amplification and detection reactions were performed as generally described above. No signal was observed with each of these samples. Similar experiments were set up by spiking a negative clinical pool with 1,000,000 copies per reaction of several other HPV transcripts at 1,000,000 copies/reaction each. HPV 31 and HPV33 amplification and detection reactions were performed as generally described above. No signal was observed with each of these samples. These data show that there is no cross-reactivity with these other HPV types and that the assay is very specific to HPV 31 and 33.

Clinical Sensitivity and Specificity

Clinical specimens (n=137) were tested in the HPV31/33 genotyping assay to assess clinical sensitivity and specificity. HPV DNA genotyping was performed with the LINEAR ARRAY HPV Genotyping Test (LA, Roche Molecular Diagnostics). This test was used as the standard to determine if a sample contained HPV31 and/or HPV33. Only a limited number of samples were available that tested HPV31 DNA positive (n=13) or HPV33 DNA positive (n=13).

Overall, with this limited data set, the clinical sensitivity for detection of HVP31 was 84.6%. Two specimens were negative in the HPV 31/33 genotyping assay that tested positive for HPV31 DNA in the LA assay. Both specimens contained HPV31 DNA along with additional HPV low risk types. Both specimens tested negative using the APTIMA HPV Screening assay, making it very unlikely that the specimens contained any HPV31 mRNA.

The clinical sensitivity for detection of HPV33 was 92.3%. One specimen was negative in the HPV 31/33 genotyping assay that tested positive for HPV33 DNA in the LA assay. This specimen contained several other high and low risk HPV DNA types. The specimen tested negative using the APTIMA HPV Screening assay and the HC2 test (Qiagen, Gaithersburg, Md.), indicating that it was unlikely this sample contained any HPV33 mRNA.

Clinical specificity for HPV31 was 98.4%. Two (2) specimens that were HPV31 negative according to the assay LA tested positive using the HPV31/33 genotyping assay. Both specimens contained additional HPV high risk types and tested positive using the APTIMA HPV Screening assay and the HC2 test (Qiagen). Specificity for HPV33 was 100%.

A summary of the clinical specimen testing results is shown in Tables 2 and 3 below.

TABLE 2

Results of clinical specimen testing for HPV31

|  |  | HPV31 according to LA assay | | |
|---|---|---|---|---|
|  |  | Positive | Negative | Total |
| HPV31 according to APTIMA 31/33 | Positive | 11 | 2 | 13 |
|  | Negative | 2 | 122 | 124 |
| GT assay | Total | 13 | 124 | 137 |

TABLE 3

Results of clinical specimen testing for HPV33

|  |  | HPV33 according to LA assay | | |
|---|---|---|---|---|
|  |  | Positive | Negative | Total |
| HPV33 according to APTIMA 31/33 | Positive | 12 | 0 | 12 |
|  | Negative | 1 | 124 | 125 |
| GT assay | Total | 13 | 124 | 137 |

Sequences

TABLE 4

Exemplary Oligomer Sequences, Reference Sequences, and Regions

| SEQ ID NO: | Sequence (5' → 3') | Description |
|---|---|---|
| 1 | TCAAGACACTGAGGAAAAACC | HPV33 Non-T7 amp oligo |
| 2 | GTTTCAAGACACTGAGGA | HPV33 Non-T7 amp oligo |
| 3 | TATGTTTCAAGACACTGAGGA | HPV33 Non-T7 amp oligo |
| 4 | ACGACTATGTTTCAAGACACTGAG | HPV33 Non-T7 amp oligo |
| 5 | GACTATGTTTCAAGACACTGAG | HPV33 Non-T7 amp oligo |
| 6 | CTGCACGACTATGTTTCAAG | HPV33 Non-T7 amp oligo |
| 7 | GTACTGCACGACTATGTTTCAAGA | HPV33 Non-T7 amp oligo |
| 8 | AGTAAGGTACTGCACGACT | HPV33 Non-T7 amp oligo |
| 9 | TAGTTGTCTCCAATGCTTG | Target hybridizing sequence (THS) of SEQ ID NO: 17 |

TABLE 4-continued

Exemplary Oligomer Sequences, Reference Sequences, and Regions

| SEQ ID NO: | Sequence (5' → 3') | Description |
|---|---|---|
| 10 | ATGTTGTGTATAGTTGTCTCC | Target hybridizing sequence (THS) of SEQ ID NO: 18 |
| 11 | TAGTTCAATGTTGTGTATAGTTGT | Target hybridizing sequence (THS) of SEQ ID NO: 19 |
| 12 | CTGTAGTTCAATGTTGTGTATAGTTG | Target hybridizing sequence (THS) of SEQ ID NO: 20 |
| 13 | GCACTGTAGTTCAATGTTGTG | Target hybridizing sequence (THS) of SEQ ID NO: 21 |
| 14 | CACGCACTGTAGTTCAATG | Target hybridizing sequence (THS) of SEQ ID NO: 22 |
| 15 | CATTCCACGCACTGTAGTTCA | Target hybridizing sequence (THS) of SEQ ID NO: 23 |
| 16 | TGCATTCCACGCACTGTAGTTCA | Target hybridizing sequence (THS) of SEQ ID NO: 24 |
| 17 | AATTTAATACGACTCACTATAGGGAGATAGTTGTCTCCAATGCTTG | HPV33 T7 amp oligo |
| 18 | AATTTAATACGACTCACTATAGGGAGAATGTTGTGTATAGTTGTCTCC | HPV33 T7 amp oligo |
| 19 | AATTTAATACGACTCACTATAGGGAGATAGTTCAATGTTGTGTATAGTTGT | HPV33 T7 amp oligo |
| 20 | AATTTAATACGACTCACTATAGGGAGACTGTAGTTCAATGTTGTGTATAGTTG | HPV33 T7 amp oligo |
| 21 | AATTTAATACGACTCACTATAGGGAGAGCACTGTAGTTCAATGTTGTG | HPV33 T7 amp oligo |
| 22 | AATTTAATACGACTCACTATAGGGAGACACGCACTGTAGTTCAATG | HPV33 T7 amp oligo |
| 23 | AATTTAATACGACTCACTATAGGGAGACATTCCACGCACTGTAGTTCA | HPV33 T7 amp oligo |
| 24 | AATTTAATACGACTCACTATAGGGAGATGCATTCCACGCACTGTAGTTCA | HPV33 T7 amp oligo |
| 25 | ATGAGCAATTACCCGACAGC | HPV31 Non-T7 amp oligo |
| 26 | GAGCAATTACCCGACAGC | HPV31 Non-T7 amp oligo |
| 27 | TACCCGACAGCTCAGATGA | HPV31 Non-T7 amp oligo |
| 28 | ACCCGACAGCTCAGATGAGG | HPV31 Non-T7 amp oligo |
| 29 | GACAGCTCAGAGGAGGAGGATG | HPV31 Non-T7 amp oligo |
| 30 | GCTCAGATGAGGAGGATGTC | HPV31 Non-T7 amp oligo |
| 31 | CAGATGAGGAGGATGTCATA | HPV31 Non-T7 amp oligo |
| 32 | ATGAGGAGGATGTCATAGACA | HPV31 Non-T7 amp oligo |
| 33 | AGGAGGATGTCATAGACAGTC | HPV31 Non-T7 amp oligo |
| 34 | CACACAAACGAAGTGTAGACTTACACTGAC | Target hybridizing sequence (THS) of SEQ ID NO: 42 |

TABLE 4-continued

Exemplary Oligomer Sequences, Reference Sequences, and Regions

| SEQ ID NO: | Sequence (5' → 3') | Description |
|---|---|---|
| 35 | GTGTAGACTTACACTGACAACA | Target hybridizing sequence (THS) of SEQ ID NO: 43 |
| 36 | CGAAGTGTAGACTTACACTGACA | Target hybridizing sequence (THS) of SEQ ID NO: 44 |
| 37 | CAAACGAAGTGTAGACTTACAC | Target hybridizing sequence (THS) of SEQ ID NO: 45 |
| 38 | CACACAAACGAAGTGTAGACT | Target hybridizing sequence (THS) of SEQ ID NO: 46 |
| 39 | CTCTGTACACACAAACGAAGT | Target hybridizing sequence (THS) of SEQ ID NO: 47 |
| 40 | GTGTGCTCTGTACACACAAACG | Target hybridizing sequence (THS) of SEQ ID NO: 48 |
| 41 | GAATATCTACTTGTGTGCTCTG | Target hybridizing sequence (THS) of SEQ ID NO: 49 |
| 42 | AATTTAATACGACTCACTATAGGGAGACACACAAACGAAGTGTAGACTTACACTGAC | HPV31 T7 amp oligo |
| 43 | AATTTAATACGACTCACTATAGGGAGAGTGTAGACTTACACTGACAACA | HPV31 T7 amp oligo |
| 44 | AATTTAATACGACTCACTATAGGGAGACGAAGTGTAGACTTACACTGACA | HPV31 T7 amp oligo |
| 45 | AATTTAATACGACTCACTATAGGGAGACAAACGAAGTGTAGACTTACAC | HPV31 T7 amp oligo |
| 46 | AATTTAATACGACTCACTATAGGGAGACACACAAACGAAGTGTAGACT | HPV31 T7 amp oligo |
| 47 | AATTTAATACGACTCACTATAGGGAGACTCTGTACACACAAACGAAGT | HPV31 T7 amp oligo |
| 48 | AATTTAATACGACTCACTATAGGGAGAGTGTGCTCTGTACACACAAACG | HPV31 T7 amp oligo |
| 49 | AATTTAATACGACTCACTATAGGGAGAGAATATCTACTTGTGTGCTC | HPV31 T7 amp oligo |
| 50 | AAAUGUUUGCUUUAUAUAUGCACC | Target hybridizing sequence (THS) of SEQ ID NO: 51 |
| 51 | AAAUGUUUGCUUUAUAUAUGCACCUUUAAAAAAAAAAAAAAAAAAAAAAAAAA | HPV33 Target capture oligo |
| 52 | GCUCAUAACAGUGGAGGUCAGUUGCCUC | Target hybridizing sequence (THS) of SEQ ID NO: 53 |
| 53 | GCUCAUAACAGUGGAGGUCAGUUGCCUCtttaaaaaaaaaaaaaaaaaaaaaaaaaa | HPV31 Target capture oligo |
| 54 | CCACGAACAUUGCAUGAUUU | HPV33 Detection probe |
| 55 | CCACGAACAUUGCAUGAUUUGUG | HPV33 Detection probe |
| 56 | CGAACAUUGCAUGAUUUGUGC | HPV33 Detection probe |
| 57 | CCACGAACAUUGCAUGAUUUGUGCC | HPV33 Detection probe |
| 58 | CGAACAUUGCAUGAUUUGUGCC | HPV33 Detection probe |

TABLE 4-continued

Exemplary Oligomer Sequences, Reference Sequences, and Regions

| SEQ ID NO: | Sequence (5' → 3') | Description |
|---|---|---|
| 59 | CAGCUGGACAAGCAGAACCGGAC | HPV31 Detection probe |
| 60 | AGCUGGACAAGCAGAACCGGAC | HPV31 Detection probe |
| 61 | AGCUGGACAAGCAGAACCGGACA | HPV31 Detection probe |
| 62 | CAGCUGGACAAGCAGAACCGGACA | HPV31 Detection probe |
| 63 | CUGGACAAGCAGAACCGGAC | HPV31 Detection probe |
| 64 | CUGGACAAGCAGAACCGGACACAUC | HPV31 Detection probe |
| 65 | CUGGACAAGCAGAACCGGACACAUCC | HPV31 Detection probe |
| 66 | AGTAAGGTACTGCACGACTATGTTTCAAGACACTGAGGAAAAACC | Amp oligo hybridizing region |
| 67 | GTTTCAAG | Amp oligo core hybridizing sequence |
| 68 | ACACTGAG | Amp oligo core hybridizing sequence |
| 69 | CTGCACGACT | Amp oligo core hybridizing sequence |
| 70 | TGCATTCCACGCACTGTAGTTCAATGTTGTGTATAGTTGTCTCCAATGCTTG | Amp oligo hybridizing region |
| 71 | CTGTAGTTC | Amp oligo core hybridizing sequence |
| 72 | ATGTTGTG | Amp oligo core hybridizing sequence |
| 73 | AGTTGTCTCC | Amp oligo core hybridizing sequence |
| 74 | ATGAGCAATTACCCGACAGCTCAGAKGAGGAGGATGTCATAGACAGTC | Amp oligo hybridizing region |
| 75 | AGGAGGATG | Amp oligo core hybridizing sequence |
| 76 | CAGAKGAGG | Amp oligo core hybridizing sequence |
| 77 | ACCCGACAGC | Amp oligo core hybridizing sequence |
| 78 | GAATATCTACTTGTGTGCTCTGTACACACAAACGAAGTGTAGACTTACACTGACAACA | Amp oligo hybridizing region |
| 79 | GTGTAGACT | Amp oligo core hybridizing sequence |
| 80 | CACACAAACG | Amp oligo core hybridizing sequence |
| 81 | TGTGCTCTG | Amp oligo core hybridizing sequence |
| 82 | AATTTAATACGACTCACTATAGGGAGA | T7 promoter sequence |
| 83 | GTAAACTATAATGCCAAGTTTTAAAAAAGTAGGGTGTAACCGAAAGCGGTTCAACCGAAAACGGTGCATATATAAAGCAAACATTTTGCAGTAAGGTACTGCACGACTATGTTTCAAGACACTGAGGAAAACCACGAACATTGCATGATTTGTGCCAAGCATTGGAGACAACTATACACAACATTGAACTACAGTGCGTGGAATGCAAAAAACCTTTGCAACGATCTGAGGTATATGATTTTGCATTTGCAGATTTAACAGTTGTATATAGAGAGGGAAATCCATTTGGAATATGTAAACTGTGTTTGCGGTTCTTATCTAAAATTAGTGAATATAGACATTATAATTATTCTGTATATGGAAATACATTAGAACAAACAGTTAAAAAACCTTTAAATG | HPV33 E6/E7 reference sequence |

TABLE 4-continued

Exemplary Oligomer Sequences, Reference Sequences, and Regions

| SEQ ID NO: | Sequence (5' → 3') | Description |
|---|---|---|
|  | AAATATTAATTAGGTGTATTATATGTCAAAGACCTTTGTG<br>TCCTCAAGAAAAAAAACGACATGTGGATTTAAACAAACGA<br>TTTCATAATATTTCGGGTCGTTGGGCAGGGCGCTGTGCGG<br>CGTGTTGGAGGTCCCGACGTAGAGAAACTGCACTGTGACG<br>TGTAAAAACGCCATGAGAGGACACAAGCCAACGTTAAAGG<br>AATATGTTTTAGATTTATATCCTGAACCAACTGACCTATA<br>CTGCTATGAGCAATTAAGTGACAGCTCAGATGAGGATGAA<br>GGCTTGGACCGGCCAGATGGACAAGCACAACCAGCCACAG<br>CTGATTACTACATTGTAACCTGTTGTCACACTTGTAACAC<br>CACAGTTCGTTTATGTGTCAACAGTACAGCAAGTGACCTA<br>CGAACCATACAGCAACTACTTATGGGCACAGTGAATATTG<br>TGTGCCCTACCTGTGCACAACAATAA |  |
| 84 | TAATAATAATAATCTTAGTATAAAAAGTAGGGAGTGACC<br>GAAAGTGGTGAACCGAAAACGGTTGGTATATAAAGCACAT<br>AGTATTTTGTGCAAACCTACAGACGCCATGTTCAAAAATC<br>CTGCAGAAAGACCTCGGAAATTGCATGAACTAAGCTCGGC<br>ATTGGAAATACCCTACGATGAACTAAGATTGAATTGTGTC<br>TACTGCAAAGGTCAGTTAACAGAAACAGAGGTATTAGATT<br>TTGCATTTACAGATTTAACAATAGTATATAGGGACGACAC<br>ACCACACGGAGTGTGTACAAAATGTTTAAGATTTTATTCA<br>AAAGTAAGTGAATTTAGATGGTATAGATATAGTGTGTATG<br>GAACAACATTAGAAAAATTGACAAACAAAGGTATATGTGA<br>TTTGTTAATTAGGTGTATAACGTGTCAAAGACCGTTGTGT<br>CCAGAAGAAAACAAAGACATTTGGATAAAAAGAAACGAT<br>TCCACAACATAGGAGGAAGGTGGACAGGACGTTGCATAGC<br>ATGTTGGAGAAGACCTCGTACTGAAACCCAAGTGTAAACA<br>TGCGTGGAGAAACACCTACGTTGCAAGACTATGTGTTAGA<br>TTTGCAACCTGAGGCAACTGACCTCCACTGTTATGAGCAA<br>TTACCCGACAGCTCAGATGAGGAGGATGTCATAGACAGTC<br>CAGCTGGACAAGCAGAACCGGACACATCCAATTACAATAT<br>CGTTACCTTTTGTTGTCAGTGTAAGTCTACACTTCGTTTG<br>TGTGTACAGAGCACACAAGTAGATATTCGCATATTGCAAG<br>AGCTGTTAATGGGCTCATTTGGAATCGTGTGCCCCAACTG<br>TTCTACTAGACTGTAA | HPV31 E6/E7 reference sequence |
| 85 | AGGAGGATGTCATAGACAAGTC | HPV31 Non-T7 amp oligo |
| 86 | AATTTAATACGACTCACTATAGGGAGAGAATATCTACTTG<br>TGTGCTC | HPV31 T7 amp oligo |
| 87 | GAATATCTACTTGTGTGCTC | Target hybridizing sequence (THS) of SEQ ID NO: 86 |
| 88 | gctcataacagtggaggtcagttgcctctttaaaaaaaaa<br>aaaaaaaaaaaaaaaaaaaa | HPV Target Capture oligomer |
| 89 | ctccaacacgctgcacagcgccctgtttaaaaaaaaaaaa<br>aaaaaaaaaaaaaaaa | HPV Target Capture oligomer |
| 90 | gtgcacagatcaggtagcttgtagggtcgtttaaaaaaaa<br>aaaaaaaaaaaaaaaaaaaa | HPV Target Capture oligomer |
| 91 | GCTCATAACAGTGGAGGTCAGTTGCCTCTTTAAAAAAAAA | HPV Target Capture oligomer |
| 92 | GCTCATAACAGTGGAGGTCAGTTGCCTC | Target hybridizing sequence (THS) of SEQ ID NO: 91 |
| 93 | GUGCACAGAUCAGGUAGCUUGUAGGGUCGUUUAAAAAAAA<br>AAAAAAAAAAAAAAAAAAAA | HPV Target Capture oligomer |
| 94 | GUGCACAGAUCAGGUAGCUUGUAGGGUCG | Target hybridizing sequence (THS) of SEQ ID NO: 93 |
| 95 | ctccaacacgctgcacagcgccctg | Target hybridizing sequence (THS) of SEQ ID NO: 89 |
| 96 | gtgcacagatcaggtagcttgtagggtcg | Target hybridizing sequence (THS) of SEQ ID NO: 90 |

TABLE 4-continued

Exemplary Oligomer Sequences, Reference Sequences, and Regions

| SEQ ID NO: | Sequence (5' → 3') | Description |
|---|---|---|
| 97 | gctcataacagtggaggtcagttgcctc | Target hybridizing sequence (THS) of SEQ ID NO: 88 |
| 98 | TTAARTGACAGCTCAGAKGAGGAKGATGAAATAGATGGTC | Amp oligo hybridizing region (HPV16) |
| 99 | CTCAGAKGAGGAKG | Amp oligo core hybridizing region (HPV16) |
| 100 | GTGACAGCTCAGATGAGGATG | HPV 16 Amp oligo |
| 101 | GACAGCTCAGAKGAGGAGGATG | HPV 16 Amp oligo |
| 102 | CTCAGAKGAGGAKGATGAAATAGATGG | HPV 16 Amp oligo |
| 103 | RTGACAGCTCAGAKGAGGAKGATG | HPV 16 Amp oligo |
| 104 | GACAGCTCAGATGAGGAGGATG | HPV 16 Amp oligo |
| 105 | TGACAGCTCAGAKGAGGAKGATGAAATAG | HPV 16 Amp oligo |
| 106 | CAATATTGTAACCTTTTGTTGCAAGTGTGACTCTACGCTTCGGTTGTGCG | Amp oligo hybridizing region (HPV16) |
| 107 | AGAGTCACACTTG | Amp oligo core hybridizing region (HPV16) |
| 108 | AATTTAATACGACTCACTATAGGGAGAACTTGCAACAAAAGGTTAC | HPV16 Amp Oligo |
| 109 | AATTTAATACGACTCACTATAGGGAGAACACTTGCAACAAAAGGTTACAATATTG | HPV16 Amp Oligo |
| 110 | AATTTAATACGACTCACTATAGGGAGAAGAGTCACACTTGCAACAAAAG | HPV16 Amp Oligo |
| 111 | AATTTAATACGACTCACTATAGGGAGAAGAGTCACACTTGCAACAAAAGG | HPV16 Amp Oligo |
| 112 | AATTTAATACGACTCACTATAGGGAGAGCACAACCGAAGCGTAGAGTC | HPV16 Amp Oligo |
| 113 | AATTTAATACGACTCACTATAGGGAGACGCACAACCGAAGCGTAGAGTCACACTTGC | HPV16 Amp Oligo |
| 114 | AATTTAATACGACTCACTATAGGGAGAAAGCGTAGAGTCACACTTGC | HPV16 Amp Oligo |
| 115 | AATTTAATACGACTCACTATAGGGAGAGCAACAAAAGGTTACAATATTG | HPV16 Amp Oligo |
| 116 | AATTTAATACGACTCACTATAGGGAGAGAAGCGTAGAGTCACACTTG | HPV16 Amp Oligo |
| 117 | CAACAAAAGGTTAC | Amp oligo core hybridizing region (HPV16) |
| 118 | ACTTGCAACAAAAGGTTAC | Target hybridizing sequence (THS) of SEQ ID NO: 104 |
| 119 | ACACTTGCAACAAAAGGTTACAATATTG | Target hybridizing sequence (THS) of SEQ ID NO: 105 |
| 120 | AGAGTCACACTTGCAACAAAAG | Target hybridizing sequence (THS) of SEQ ID NO: 106 |

TABLE 4-continued

Exemplary Oligomer Sequences, Reference Sequences, and Regions

| SEQ ID NO: | Sequence (5' → 3') | Description |
|---|---|---|
| 121 | AGAGTCACACTTGCAACAAAAGG | Target hybridizing sequence (THS) of SEQ ID NO: 107 |
| 122 | GCACAACCGAAGCGTAGAGTC | Target hybridizing sequence (THS) of SEQ ID NO: 108 |
| 123 | CGCACAACCGAAGCGTAGAGTCACACTTGC | Target hybridizing sequence (THS) of SEQ ID NO: 109 |
| 124 | AAGCGTAGAGTCACACTTGC | Target hybridizing sequence (THS) of SEQ ID NO: 110 |
| 125 | GCAACAAAAGGTTACAATATTG | Target hybridizing sequence (THS) of SEQ ID NO: 111 |
| 126 | GAAGCGTAGAGTCACACTTG | Target hybridizing sequence (THS) of SEQ ID NO: 112 |
| 127 | CAGCKGGACAAGCAGAACCGGAC | Detection probe (HPV16) |
| 128 | CGACGAGCCGAACCAC | HPV18 Amp Oligo |
| 129 | CGACGAGCCGAACCACA | HPV18 Amp Oligo |
| 130 | GACGAGCCGAACCACA | HPV18 Amp Oligo |
| 131 | CGACGAGCCGAACCACAA | HPV18 Amp Oligo |
| 132 | GACGAGCCGAACCACAA | HPV18 Amp Oligo |
| 133 | ACGAGCCGAACCACAA | HPV18 Amp Oligo |
| 134 | AATTTAATACGACTCACTATAGGGAGAGTTCAGAAACAGCTGCTGG | HPV18 Amp Oligo |
| 135 | AATTTAATACGACTCACTATAGGGAGAGTGTTCAGAAACAGCTGCTGG | HPV18 Amp Oligo |
| 136 | AATTTAATACGACTCACTATAGGGAGAGGGTGTTCAGAAACAGCTGCTGG | HPV18 Amp Oligo |
| 137 | AATTTAATACGACTCACTATAGGGAGAGGGTGTTCAGAAACAGCTG | HPV18 Amp Oligo |
| 138 | AATTTAATACGACTCACTATAGGGAGAACACACAAAGGACAGGGT | HPV18 Amp Oligo |
| 139 | AATTTAATACGACTCACTATAGGGAGAGACACACAAAGGACAGGGT | HPV18 Amp Oligo |
| 140 | AATTTAATACGACTCACTATAGGGAGAGCACACCACGGACACACAAAGG | HPV18 Amp Oligo |
| 141 | AATTTAATACGACTCACTATAGGGAGACACACCACGGACACACAAGGAC | HPV18 Amp Oligo |
| 142 | AATTTAATACGACTCACTATAGGGAGACACACCACGGACACACAAAG | HPV18 Amp Oligo |
| 143 | CCAGCAGCTGTTTCTGAACACCCTGTCCTTTGTGTGTCCGTGGTGTGC | Hyb region 18 |
| 144 | GTTCAGAAACAGCTGCTGG | Target hybridizing sequence (THS) of SEQ ID NO: 134 |

TABLE 4-continued

Exemplary Oligomer Sequences, Reference Sequences, and Regions

| SEQ ID NO: | Sequence (5' → 3') | Description |
|---|---|---|
| 145 | GTGTTCAGAAACAGCTGCTGG | Target hybridizing sequence (THS) of SEQ ID NO: 135 |
| 146 | GGGTGTTCAGAAACAGCTGCTGG | Target hybridizing sequence (THS) of SEQ ID NO: 136 |
| 147 | GGGTGTTCAGAAACAGCTG | Target hybridizing sequence (THS) of SEQ ID NO: 137 |
| 148 | ACACACAAAGGACAGGGT | Target hybridizing sequence (THS) of SEQ ID NO: 138 |
| 149 | GACACACAAAGGACAGGGT | Target hybridizing sequence (THS) of SEQ ID NO: 139 |
| 150 | GCACACCACGGACACACAAAGG | Target hybridizing sequence (THS) of SEQ ID NO: 140 |
| 151 | CACACCACGGACACACAAAGGAC | Target hybridizing sequence (THS) of SEQ ID NO: 141 |
| 152 | CACACCACGGACACACAAAG | Target hybridizing sequence (THS) of SEQ ID NO: 142 |
| 153 | GCAGACGACCUUCGAGCAUUC | Detection probe (HPV18) |
| 154 | CGUCUGCUGAGCUUUCUA | Detection probe (HPV18) |
| 155 | GUAGUAGAAAGCUCAGCAGACGACC | Detection probe (HPV18) |
| 156 | GUAGAAACCUCGC | Detection probe (HPV18) |
| 157 | GUAGAGAGCUCGGCAGANGAC | Detection probe (HPV18) |
| 158 | GUGUGACGGCAGAAUUGAGC | Detection probe (HPV18) |
| 159 | UGUGUGUGUGUUGUAAGUGU | Detection probe (HPV18) |
| 160 | UCUUCUGCCGAGCUC | Detection Probe |
| 161 | GUAGAGAGCUCGGCAGAGGAC | Detection Probe |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. An oligomer combination for detecting a human papillomavirus type 33 (HPV33) target nucleic acid and a human papillomavirus type 31 (HPV31) in a sample suspected of containing HPV33 and/or HPV31 and at least one of HPV types 52, and 58, said oligomer combination comprising:
   first and second amplification oligomers for specifically amplifying an HPV33 nucleic acid target region, wherein
   (a) the first HPV33 amplification oligomer comprises a first target-hybridizing sequence that is from 15 to 27 contiguous nucleotides in length and is contained in the sequence of SEQ ID NO:66 and that includes the sequence of SEQ ID NO:67 or SEQ ID NO:69; and
   (b) the second HPV33 amplification oligomer is a promoter primer or a promoter provider comprising (i) a second target-hybridizing sequence, wherein the second target hybridizing sequence is from 15 to 27 contiguous nucleotides in length and is contained in the sequence of SEQ ID NO:70 and includes the sequence of SEQ ID NO:72 or SEQ ID NO:73; and (ii) a promoter sequence joined to 5' end of the second target-hybridizing sequence; and
   first and second amplification oligomers for specifically amplifying an HPV type 31 (HPV31) nucleic acid target region, wherein
   (c) the first HPV31 amplification comprises a first target-hybridizing sequence that is from 15 to 27 contiguous nucleotides in length and is contained in the sequence of SEQ ID NO:74 and that includes at least the sequence of SEQ ID NO:75, SEQ ID NO:76, or SEQ ID NO:77; and
   (d) the second HPV31 amplification oligomer is a promoter primer or a promoter provider comprising (i) a second target-hybridizing sequence, wherein the second target hybridizing sequence is from 15 to 30 contiguous nucleotides in length and is contained in the sequence of SEQ ID NO:78 and includes at least the sequence of SEQ ID NO:79, SEQ ID NO:80, or SEQ ID NO:81; and (ii) a promoter sequence joined to 5' end of the second target-hybridizing sequence.

2. The oligomer combination of claim 1,
   wherein the promoter sequence of the second HPV33 oligomer is a T7 promoter sequence; or,
   wherein the T7 promoter sequence has the sequence shown in SEQ ID NO:82.

3. The oligomer combination of claim 1,
   wherein the promoter sequence of the second HPV31 oligomer is a T7 promoter sequence; or,
   wherein the T7 promoter sequence has the sequence shown in SEQ ID NO:82.

4. The oligomer combination claim 1, further comprising at least one HPV33 detection probe oligomer comprising a target-hybridizing sequence that is from about 14 to about 35 nucleotides in length and is configured to specifically hybridize to a target sequence contained within SEQ ID NO:83 from about nucleotide position 128 to about nucleotide position 164; or,
   wherein the HPV33 detection probe target-hybridizing sequence is selected from the group consisting of SEQ ID NOs:54-58.

5. The oligomer combination claim 1, further comprising at least one HPV31 detection probe oligomer comprising a target-hybridizing sequence that is from about 14 to about 40 nucleotides in length and is configured to specifically hybridize to a target sequence contained within SEQ ID NO:84 from about nucleotide position 675 to about nucleotide position 735; or,
   wherein the HPV31 detection probe target-hybridizing sequence is selected from the group consisting of SEQ ID NOs:59-65.

6. A kit or a reaction mixture comprising the oligomer combination of any of claims 1 and 2 to 5.

7. A method for detecting a human papillomavirus type 33 (HPV33) target nucleic acid in a sample suspected of containing HPV33 and at least one of HPV types 31, 52, and 58, said method comprising:
   (a) providing a sample, wherein said sample is suspected of containing HPV33 and at least one of HPV types 31, 52, and 58;
   (b) contacting the sample with the oligomer combination according to claim 1;
   (c) performing an in vitro nucleic acid amplification reaction, wherein any HPV33 target nucleic acid present in said sample is used as a template for generating an HPV33 amplification product; and
   (d) detecting the presence or absence of the HPV33 amplification product, thereby indicating the presence or absence of HPV33 in said sample.

8. The method of claim 7,
   wherein the promoter sequence of the second HPV33 oligomer is a T7 promoter sequence; or, wherein the T7 promoter sequence has the sequence shown in SEQ ID NO:82.

9. The method of claim 7, wherein the promoter sequence of the second HPV31 oligomer is a T7 promoter sequence; or, wherein the T7 promoter sequence has the sequence shown in SEQ ID NO:82.

\* \* \* \* \*